(12) United States Patent
Arai et al.

(10) Patent No.: US 6,780,597 B1
(45) Date of Patent: Aug. 24, 2004

(54) NF-AT DERIVED POLYPEPTIDES THAT BIND CALCINEURIN AND USES THEREOF

(75) Inventors: Ken-ichi Arai, Tokyo (JP); Jie Liu, Mountain View, CA (US)

(73) Assignee: Center for Advanced Science and Technology Incubation, Ltd., Tokyo (JP)

( * ) Notice: Subject to any disclaimer, the term of this patent is extended or adjusted under 35 U.S.C. 154(b) by 0 days.

(21) Appl. No.: 09/550,115

(22) Filed: Apr. 14, 2000

(51) Int. Cl.$^7$ ............................................... G01N 33/53
(52) U.S. Cl. ............................ 435/7.1; 435/4; 530/350
(58) Field of Search .............................. 530/324; 435/4, 435/7.1, 21

(56) References Cited

PUBLICATIONS

Ho et al. J. Biol. Chem. 270, 19898–19907 (1995).*
E. S. Masuda et al., Cell. Signal, "Signalling into the T–Cell Nucleus: NFAT Regulation," vol. 10, No. 9, pp. 599–611 (1998).
E. s. Masuda et al., Molecular and Cellular Biology. "NFATx, a Novel Member of the Nuclear Factor of Activated T Cells Family That Is Expressed Predominantly in the Thymus," vol. 15, No. 5, pp. 2697–2706 (1995).
E. s. Masuda et al., Molecular and Cellular Biology, "Control of NFATx1 Nuclear Translocation by a Calcineurin–Regulated Inhibitory Domain," vol. 17, No. 4, pp. 2066–2075 (1997).
C. R. Beals et al., Genes & Development, "Nuclear localization of NF–Atc by a calcineurin–dependent, cyclosporin–sensititve intramolecular interaction," vol. 11, pp. 824–834 (1997).
C. Luo et al., Proc. Natl. Acad. Sci. USA, "Interaction of calcineurin with a domain of the transcription factor NFAT1 that controls nuclear import," vol. 93, pp. 8907–8912 (1996).
J Liu et al., Molecular Biology of the Cell, "Calcineurin–dependent Nuclear Translocation of a Murin Transcription Factor NFATx: Molecular Cloning and Functional Characterization," vol. 8, pp. 157–170 (1997).
J. Aramburu et al., Molecular Cell, "Selective Inhibition of NFAT Activation by a Peptide Spanning the Calcineurin Targeting Site of NFAT," vol. 1, pp. 627–637 (1998).
J. Zhu et al., Cell, "Intramolecular Masking of Nuclear Import Signal on NF–AT4 by Casein Kinase I and MEKK1," vol. 93, pp. 851–861 (1998).
J. Liu et al., The Journal of Immunology, Two Independent Calcineurin–Binding Regions in the N–Terminal Domain of Murine NF–ATx1 Recruit Calcineurin to Murine NF–ATx1, pp. 4755–4761 (1999) The American Association of Immunologists.

* cited by examiner

*Primary Examiner*—Robert A. Wax
(74) *Attorney, Agent, or Firm*—Foley & Lardner LLP

(57) ABSTRACT

Calcineurin (CN)-binding regions in the N-terminal domain derived from NF-ATx is disclosed. Also disclosed are CN-binding polypeptide compositions, DNA segments encoding these polypeptides, and methods of use. The CN-binding polypeptides bind to CN, suppressing the interaction between NF-AT and CN. The CN-binding polypeptide compositions can be used for treating pharmacological intervention with $Ca^{2+}$-dependent signaling events. The CN-binding polypeptide or DNA segments encoding them can be used to assay and screen candidates of pharmaceuticals, in particular, in the evaluation and characterization of immunosuppressants specifically interfering with the interaction between NF-AT and CN.

6 Claims, 11 Drawing Sheets

Figure 10

```
                          CNBR1
mNFATx    1   MTTANCGAHDELDFKLVFGEDGAPAPPPPGSRPADLEPDDCASIYIFNVDPPPSTLTTPLCLPHHGL-PSHSSVLSPSFQ   79
hNFATx    1   ........................................................................   79
NFATc3    1   .....................PRRVLFSVSA.QL.SRTR.PSDL...........NSS.G........LQ.-    69 mNFATx   80   LQSHKNYEGTCEIPESKYSPLGGPKPFECPSIQFTSISPNCQQELDAHEDDLQINDPEREFLERPSRDHLYLPLEPSYRE  159
hNFATx   80   ..................................I......H.............................        159
NFATc3   70   ..GY......GD.S...................I........H.GT.......Y...                       149 mNFATx  160   SSLSPSPASSISSRSWFSDASSCESLSHIYDDVDSELNEAAARFTLGSPLTSPGGSPGGCPGEESWHQQYGSGHSLSPRQ  239
hNFATx  160   ........................................................T.....L........        239
NFATc3  150   ........................................................                       229 mNFATx  240   SPCHSPRSSITDENWLSPRPASGPSSRPTSPCGKRRHSSAEVCYAGSLSPHHSPVPSPGHSPRGSVTEDTWLTAPVHTGS  319
hNFATx  240   .........V.....................................................N.S..G.         319
NFATc3  230   ........................................................                       309

CNBR2
mNFATx  320   GLSPAPFPFQYCVETDIPLKTRKTSEDQAAILPGKLEICSDDQGNLSPSRETSVDDGLGSQYPLKKDSSGDQFLSVPSPF  399
hNFATx  320   ...G.V..........................L......S.A..I..........C......                  399
NFATc3  310   ........................................                                       389 mNFATx  400   TWSKPKPGHTPIFRTSSLPPLDWPLPTHFGQCELKIEVQPKTHHRAHYETEGSRGAVKASTGGHPVVKLLGYSEKPINLQ  479
hNFATx  400   ........................A.........................................N.....       479
NFATc3  390   ........................                                                        469 mNFATx  480   MFIGTADDRYLRPHAFYQVHRITGKTVATASQEIIIASTKVLEIPLLPENNMSASIDCAGILKLRNSDIELRKGETDIGR  559
hNFATx  480   ........................................................                       479
NFATc3  470   ........................                                                        469
```

Figure 11

NF-AT DERIVED POLYPEPTIDES THAT BIND CALCINEURIN AND USES THEREOF

FIELD OF THE INVENTION

This invention relates to novel polynucleotides, polypeptides encoded by them, use of the polynucleotides and polypeptides, and a method for producing them. More particularly, the present invention relates to Calcineurin (CN)-binding polypeptides.

BACKGROUND OF THE INVENTION

The calcium/calmodulin-dependent serine/threonine phosphatase, Calcineurin (CN) (Masuda, E. S. et al., 1999, Cell. Signaling 10:599), is a heterodimeric protein composed of a calmodulin-binding catalytic subunit, CNA, and a $Ca^{2+}$-binding regulatory subunit, CNB (Kincaid, R. 1993, Adv. Second Messenger Phosphoprotein Res. 27:1). CN is a target of the immunosuppressive drugs cyclosporin A (CSA) and FK506, which block T cell function by preventing transcriptional activation of cytokine genes. It has been suggested that CN plays an essential role in calcium-dependent dephosphorylation signal transduction pathways and subsequently leads to production of cytokines in T cells (Crabtree, G. R., and N. A. Clipstone, 1994, Annu. Rev. Biochem. 63:1045). Further studies have revealed that the potential of CN to regulate the expression of cytokine genes is largely due to effects on activation of a transcription factor termed nuclear factor of activated T cells (NF-AT) (Rao, A. et al., 1997, Annu. Rev. Immunol. 15:707; Masuda, E. S. et al., 1999, Cell. Signaling 10:599).

Currently, five NF-AT family members (NF-AT1/NF-ATp, NF-ATc/NF-AT2, NF-ATx/NF-AT4/NF-ATc3, NF-AT3, and TonE-BP/NF-AT5) have been identified, and they share functional and structural similarities (Hoey, T. et al., 1995, Immunity 2:461; Masuda, E. S. et al., 1995, Mol. Cell. Biol. 15:2697; McCaffrey, P. G. et al., 1993, Science 262:750; Northrop, J. P. et al., 1994, Nature 369:497; Miyakawa, H. et al., 1999, Proc. Natl. Acad. Sci. USA 96: 2538–42; Lopez-Rodriguez, C. et al., 1999, Proc. Natl. Acad. Sci. USA 96: 7214–9). The NF-AT complex is composed of at least two components. Both activation of the protein kinase C/Ras pathway and the elevated level of intracellular calcium are required for activation of this complex. The former is responsible for formation of the AP1 (activating protein-1) complex, as the nuclear components of NF-AT, while the latter leads to translocation of NF-AT from the cytoplasm to the nucleus, where it binds with AP1 at IL-2 promoter NF-AT sites (Crabtree, G. R., and N. A. Clipstone, 1994, Annu. Rev. Biochem. 63:1045; Rao, A. 1994, Immunol. Today 15:274). Thus, nuclear transport is a critical step that allows NF-AT to function in the nucleus. CN has been shown to dephosphorylate NF-AT, the result being nuclear translocation of NF-AT (Karen, T.-Y. S. et al., 1995, Natl. Acad. Sci. USA 92:11205), which can be inhibited by and FK506 (Bierer, B. E. 1994, Chem. Immunol. 59:128).

NF-AT protein is functionally divided into three domains. First, the Rel similarity domain (RSD) has a high sequence homology among different family members. It is responsible for DNA binding and cooperatively interacts with AP1 proteins (Hoey, T. et al., 1995, Immunity 2:461; McCaffrey, P. G. et al., 1993, Science 262:750; Jain, J. et al., 1995, J. Biol. Chem. 270:4138). In addition, one of the two putative conserved nuclear localization signals (NLSs) present in NF-AT family members is located within RSD (Hoey, T. et al., 1995, Immunity 2:461; Masuda, E. S. et al., 1995, Mol. Cell. Biol. 15:2697; McCaffrey, P. G. et al., 1993, Science 262:750; Northrop, J. P. et al., 1994, Nature 369:497). Second, a C-terminal domain eliciting less sequence homology has been reported to bear a transactivation motif (Imamura, R. et al., 1998, J. Immunol. 161:3455). The third domain showing homology among NF-AT proteins is the N-terminal domain. Several conserved motifs, such as SP boxes that are rich in serines and prolines (Masuda, E. S. et al., 1995, Mol. Cell. Biol. 15:2697), CN-regulated inhibitory (CRI) sequence/serine-rich region (SRR) (Masuda, E. S. et al., 1997, Mol. Cell. Biol. 17:2066; Beals, C. R. et al., 1997, Genes Dev. 11:824), and another functional NLS (Beals, C. R. et al., 1997, Genes Dev. 11:824; Luo, C. et al., 1996, Proc. Natl. Acad. Sci. USA 93:8907), have been identified within the N-terminal domain. The conserved serine residues in the SRR motif were found to be constitutively phosphorylated by cellular kinases and can be dephosphorylated by CN (Beals, C. R. et al., 1997, Genes Dev. 11:824). Deletion of CRI in human NF-ATx1 (hNF-ATx1) or mutation of serines in the SRR motif of NF-ATc led to the constitutive nuclear translocation of either hNF-ATx1or NF-ATc (Masuda, E. S. et al., 1997, Mol. Cell. Biol. 17:2066; Beals, C. R. et al., 1997, Genes Dev. 11:824). Furthermore, at least two conserved NLSs have been reported to be essential for the nuclear translocation of NF-ATc; one NLS located in RSD is associated with the majority of phosphorylated serines in SRR (Beals, C. R. et al., 1997, Genes Dev. 11:824). Thus, NLS is probably masked by these phosphorylated serine residues. Both the domain interacting with CN and residues dephosphorylated by CN have been mapped within the N-terminus of NF-AT (Masuda, E. S. et al., 1995, Mol. Cell. Biol. 15:2697; Beals, C. R. et al., 1997, Genes Dev. 11:824; Luo, C. et al., 1996, Proc. Natl. Acad. Sci. USA 93:8907), suggesting that the N-terminal domain of NF-AT is a target of CN action involved in major activities of the $Ca^{2+}$ signaling pathway and is important for the nuclear localization of NF-AT. However, detailed interaction between CN and NF-AT has not been clarified.

SUMMARY OF THE INVENTION

Structural and functional analyses of the N-terminal domain of murine NF-ATx1 (mNF-ATx1), (Liu, J. et al., 1997, Mol. Biol. Cell. 8:157), a member of the NF-AT family, have defined two distinct CN binding regions (CNBRs), CNBR1 and CNBR2, which are located in the region preceding the SP boxes of serine/proline-rich sequences and the region between the SP boxes and Rel similarity domain, respectively. Each of the two CN binding regions has the capacity to independently bind CN. The binding of mNF-ATx1 to CN was abolished by deletion of these two regions, yet was unaffected by the individual deletion. In contrast, the nuclear translocation of mNF-ATx1 was much reduced when only CNBR2 was removed. Luciferase assay revealed that both regions are required for mNF-ATx1-dependent activation of the murine IL-2 promoter. Most importantly, recombinant CNBR2 bound CN with a higher affinity, and when expressed in Jurkat cells, it functioned as a dominant negative mutant that prevented the transcription driven by exogenous mNF-ATx1, probably by interfering with the function of CN. The present invention revealed important features of the interaction of mNF-ATx1 with CN via the CN binding region, and light was shed on a structure-function model of mNF-ATx1 proteins. The finding that one of two CN binding regions acts as an inhibitor of mNF-ATx1 opens the way for development of immunosuppressive agents. The present invention provides a new opportunity for pharmacological intervention with $Ca^{2+}$-dependent signaling events.

In one aspect, the invention relates to CN binding polypeptides and DNAs encoding them, and methods for their production.

Another aspect of the invention relates to methods for using polypeptides and polynucleotides of the invention. In particular, the present invention relates to a method for screening a compound that inhibits interation between NF-AT and CN using the polypeptides of the present invention.

Still another aspect of the present invention is pharmaceutical compositions comprising a polypeptide of the present invention or a compound isolable by the above screening method. The pharmaceutical compositions can be used to inhibit interaction between NF-AT and CN. CN/NF-AT signal transduction is involved in induction of an immune response. Immunoreaction can thus be suppressed by inhibiting interaction between NF-AT and CN. The pharmaceutical compositions of this invention are especially useful for suppressing rejection after transplantation of organs and treating or preventing autoimmune diseases. The polypeptides of this invention are useful for preventing hypercardia and hypertrophy of the vascular wall.

More specifically, the present invention relates to:

(1) a polypeptide having Calcineurin-binding activity selected from the group consisting of:
   (a) polypeptides comprising the amino acid sequence set forth in SEQ ID NO: 1 (CNBR1: positions 25 to 142 of mNF-ATx1) or SEQ ID NO: 2 (CNBR2: positions 321 to 406 of mNF-ATx1);
   (b) polypeptides corresponding to the polypeptides of (a) contained in NF-Atx family proteins;
   (c) polypeptides of (a) or (b) in which one or more amino acids are added, deleted, substituted, and/or inserted; and
   (d) fusion polypeptides comprising a polypeptide of (a), (b) or
   (c) and one or more other polypeptides;

(2) a DNA encoding the polypeptide of (1);
(3) a vector comprising the DNA of (2);
(4) a transformant carrying the DNA of (2) or the vector of (3);
(5) a method for producing the polypeptide of (1), the method comprising culturing the transformant of (4), and recovering the expressed polypeptide from the transformant or the culture supernatant;
(6) a method for screening a compound that inhibits the interaction between Calcineurin and NF-AT, the method comprising:
   (a) contacting the polypeptide of (1) with Calcineurin in the presence or absence of a sample;
   (b) detecting the binding activity of the polypeptide to Calcineurin; and
   (c) selecting a compound that reduces the binding activity compared to the binding activity detected in the absence of a sample;
(7) a compound isolable by the screening method of (6);
(8) a pharmaceutical composition comprising the compound of (7) as an active ingredient;
(9) a pharmaceutical composition comprising the polypeptide of (1) as an active ingredient;
(10) a method of suppressing immune, the method comprising administering the pharmaceutical composition of (8) to a patient in need of immunosuppression; and
(11) a method of suppressing immune, the method comprising administering the pharmaceutical composition of (9) to a patient in need of immunosuppression.
(12) a method of preventing the hypertrophy of cardiac smooth muscle or vascular smooth muscle, the method comprising administering the pharmaceutical composition of (8) to a patient.
(13) a method of preventing the hypertrophy of cardiac smooth muscle or vascular smooth muscle, the method comprising administering the pharmaceutical composition of (9) to a patient.

BRIEF DESCRIPTION OF THE DRAWINGS

FIG. 10 shows the alignment of amino acid sequences in N-terminal domains of NF-ATx polypeptide family. mNFATx; mouse NFATx (SEQ ID NO: 5) hNFATx (SEQ ID NO: 6); human NFATx, NFATc3 (SEQ ID NO. 7); human and mouse NFATc3.

FIG. 11 shows the alignment of amino acid sequences (SEQ ID NOS 8–11, respectively, in order of appearance) in N-terminal domains of human members of the NFAT polypeptide family. Sequences for NFAT1 (Luo, C. E. et al., 1996, Mol. Cell. Biol. 16: 3955–66), NFATc (Northrop, J. P. et al., 1994, Nature 369:497–5021, NFATx (Hoey, T. et al., 1995, Immunity 2: 461–72; Masuda, E. S. et al., 1995, Mol. Cell. Biol. 15: 2697–706), and NFAT3 (Hoey, T. et al., 1995, Immunity 2:461–72) were aligned by using the Lasergene Megalign program (DNAstar, Madison, Wis.), with additional adjustments. Residues are numbered on the right and end at sequences corresponding to the start of their RSDs. Consensus residues, shown above the alignment, are a 100% match for the residue group. Residue groupings were as follows: DE; HKR; AGILV; NQ; FWY; ST; P; CM. Residues that match the consensus are shaded (with solid black).

DETAILED DESCRIPTION OF THE INVENTION

The present invention is described below. All the patents, publications, and literature references described herein are incorporated by reference.

Figure 3:
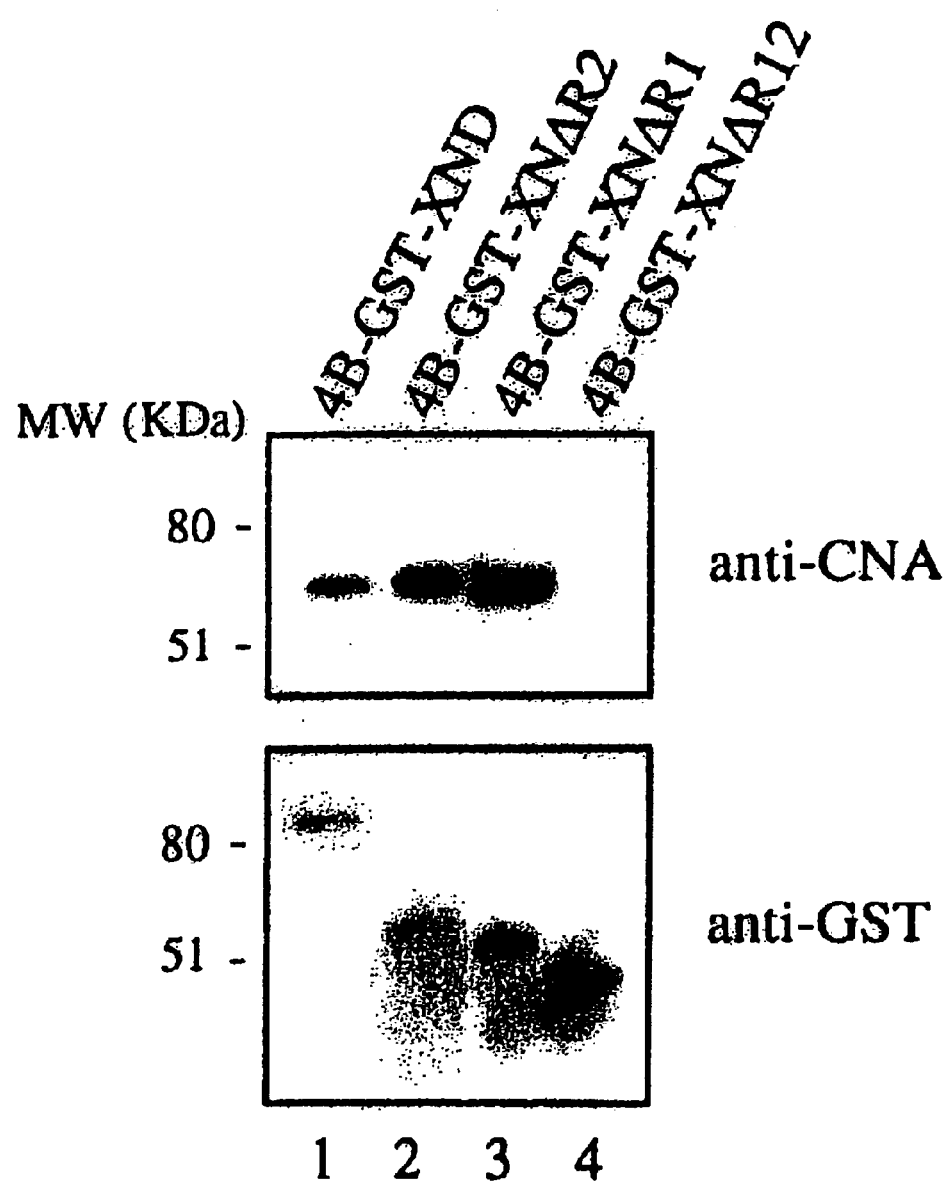
FIG. 3 shows the CN binding activities of different mNF-ATx1 GST fusion proteins. Equal amounts of COS-7 cell lysates that had been transfected with pBJ5-CNA and pBJ5-CNB were incubated with glutathione-Sepharose 4B-bound GST fusion proteins of XND (lane 1), XNΔR2 (lane 2), XNΔR1 (lane 3), or XNΔR12 (lane 4). CN binding assays were performed under the same conditions as those described in FIG. 1. Size markers are shown in kilodaltons on the left.

$Ca^{2+}$ signal- and NF-AT-dependent transactivation is a complex process. NF-AT rapidly translocates into the nucleus upon $Ca^{2+}$ signaling, an event prevented by CsA and FK506 and hence requiring the action of CN. Association between CN and NF-AT1/NF-ATx/4 has been reported (Masuda, E. S. et al., 1997, Mol. Cell. Biol. 17:2066; Luo, C. et al., 1996, Proc. Natl. Acad. Sci. USA 93:8907; Aramburu, J. et al., 1998, Mol. Cell 1:627). Present invention describes identification and characterization of the CN binding regions in NF-AT. Using a series of truncated mNF-ATx1 proteins carrying a different N-terminal portion, the inventors identified two distinct CN binding regions responsible for mNF-ATx1 interacting with CN. Removal of either region alone did not abolish CN binding of mNF-ATx1, but deletion of both regions did so (FIG. 3). These results are consistent with the previous data that multiple. CN binding sites are present in the N-terminal domain of human NF-ATx1 (hNF-ATx1) and contribute to hNF-ATx1-CN interactions (Masuda, E. S. et al., 1997, Mol. Cell. Biol. 17:2066).

Figure 1:
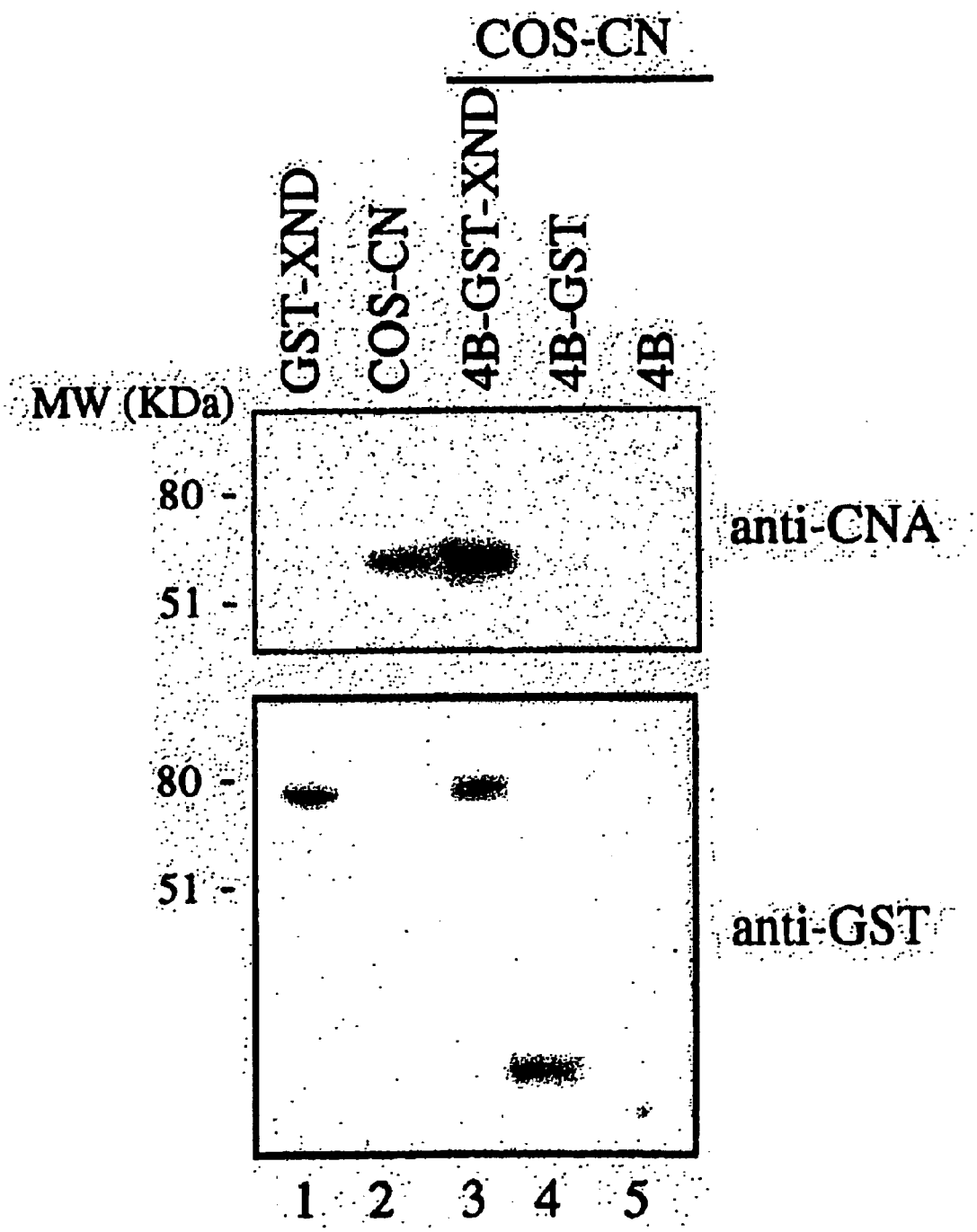
FIG. 1 shows that CN interacts with the N-terminal domain of mNF-ATx1. Equal amounts of cell lysates isolated from pBJ5-CNA and pBJ5-CNB transfected COS-7 cello were incubated in the presence of glutathione-Sepharose 4B-bound GST-XND fusion protein (lane 3), glutathione-Sepharose 4B-bound GST alone (lane 4), and glutathione-Sepharose 4B alone (lane 5). Following binding and washing, the bound fraction was eluted and analyzed by SDS-PAGE and examined by Western blotting using either anti-CNA (upper panel) or anti-GST Ab (lower panel). In lanes 1 and 2, purified GST-XND fusion protein and the cell lysate isolated from CN-transfected COS-7 cells were subjected to SDS-PAGE directly for Western blotting assay, as the controls. Size markers are shown in kilodaltons on the left.

Like other NF-AT family members, the N-terminal domain of mNF-ATx1 is rich in serine/proline residues and appears to play an important role in controlling the subcellular localization of NF-AT (Rao, A. et al., 1997, Annu. Rev. Immunol. 15:707; Masuda, E. S. et al., 1999, Cell. Signaling 10:599). As demonstrated in the CN binding assay, GST-XND fusion protein that had been incubated with the cell lysates of CNA/B-transfected COS cells migrated slightly slower than in the absence of the cell lysates (FIG. 1, compare lane 1 with lane 3). It is likely that the change in mobility is due to a phosphorylation of this protein by kinase(s) existing in COS-7 cells.

Figure 4:
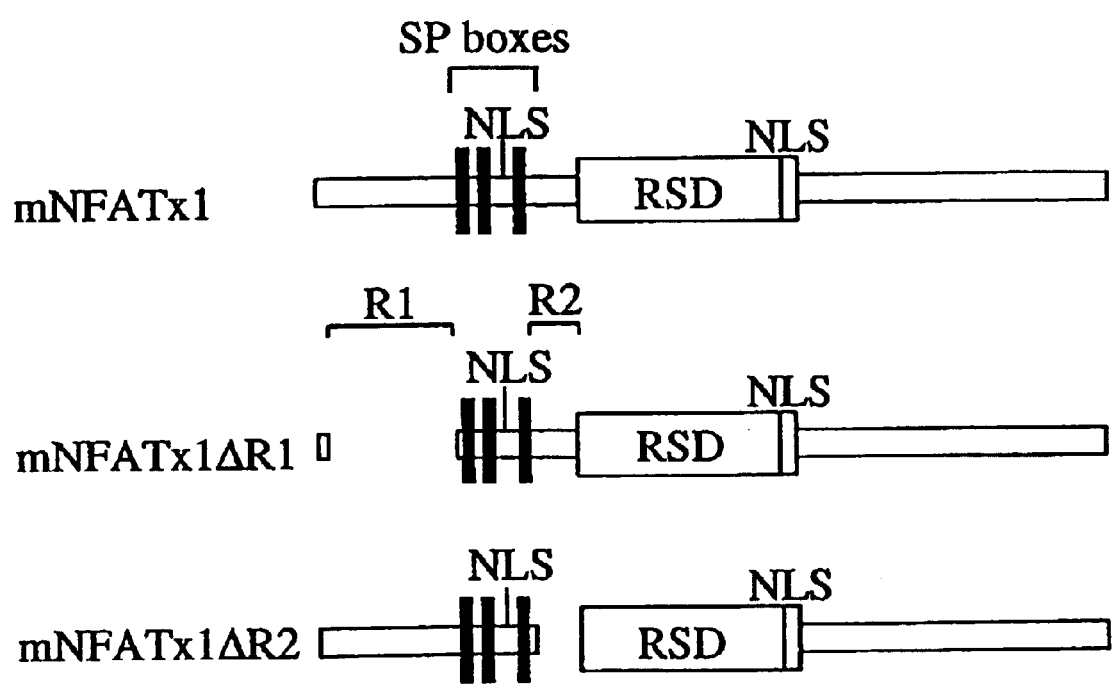
FIG. 4 schematically shows the N-terminal deletion mutants of mNF-ATx1. mNF-ATx1ΔR1 and mNF-ATx1ΔR2 were prepared by deleting R1 and R2, respectively, in the N-terminal domain of mNF-ATx1, as described in EXAMPLES. The SP boxes, NLSs, and RSD are indicated.
Figure 8:
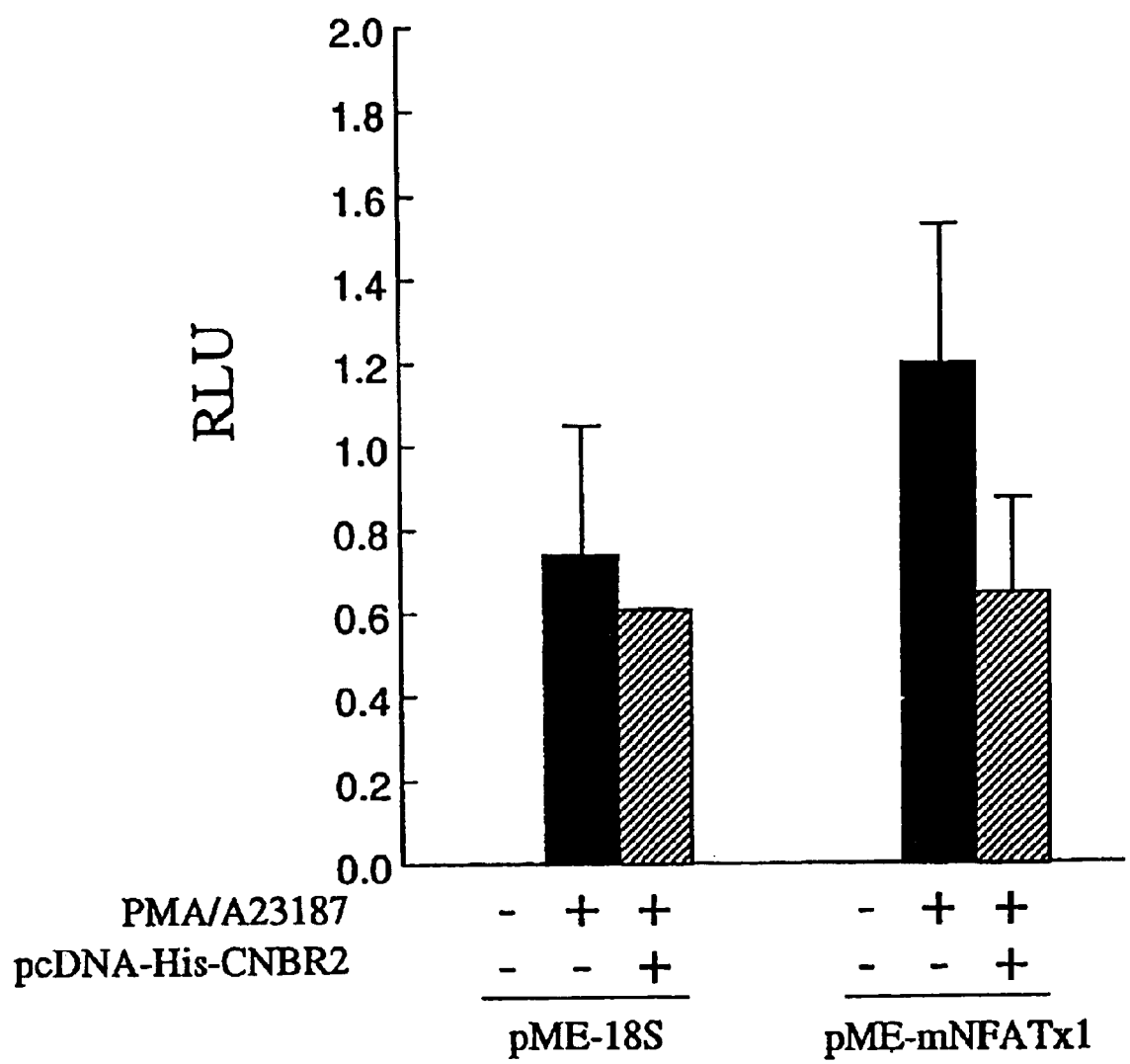
FIG. 8 shows that recombinant CNBR2 suppresses mNF-ATx1-mediated transcription activity. Jurkat cells were transfected with pNF-AT72Luc reporter and pCMV-SEAP with pME-18S or pME-mNF-ATx1 alone or together with pcDNA-His-CNBR2. The empty expression vector pcDNA3.1/His was used to adjust the total amount of DNA transfected in each transfection, as required, and was used as a control. The transfected cells were either unstimulated or stimulated with PMA/A23187 for 8 h. In all transfections, pCMV/SEAP was included to monitor transfection efficiency. Luciferease activity values, given in relative luciferase units (RLU), were normalized to protein amounts in the lysates and to transfection efficiency. The data shown here were derived from three independent transfection experiments.

Among the CNBRs of mNF-ATx1 identified herein, CNBR2 (extending 86 amino acid residues located between the SP boxes and the RSD of mNF-ATx1) has unique properties. First, the CNBR2 fusion protein showed a strong binding activity to CN. Second, only when CNBR2 was removed from mNF-ATx1 was the nuclear translocation of mNF-ATx1 severely impaired (FIGS. 4 and 5), even although CNBR1 was present. Most recently, the CN binding site of C/CM2 sequence was mapped within the corresponding region of CNBR1 in NF-AT1 and NF-AT4 molecules, respectively (FIG. 9) (Aramburu, J. et al., 1998, Mol. Cell 1:627; Zhu, J. et al., 1998, Cell 93:851). The sequence of this putative CN binding site was also noted and conserved in CNBR1 of mNF-ATx1 protein, suggesting that CNBR1 might be commonly used among the different NF-AT family members for CN interaction. In contrast to the present invention, their results showed a constitutively cytoplasmic localization of NF-AT4 and NF-AT1 when this CN binding site was deleted. In one assay system described herein, CNA and CNB were overexpressed during cotransfection with mNF-ATx1 deletion mutants, thus possibly overcoming the requirement of CNBR1 for mNF-ATx1 and transport mNF-ATx1ΔR1 to the nucleus through interaction with CNBR2. Likewise, Zhu et al. found that when coexpressed with CN, the NF-AT4 mutant, in which the C sequence (putative CN binding site) was deleted, translocated into the nucleus upon activation of $Ca^{2+}$ signaling pathway (Zhu, J. et al., 1998, Cell 93:851). It is noteworthy that although the nuclear translocation of mNF-ATx1 was impaired dramatically by deleting CNBR2 (FIG. 5), it was not blocked completely; the mNF-ATx1ΔR2 molecule was present in the nucleus of approximately 10% of transfected cells upon activation (data not shown). It appears that CNBR1 may play a lesser role in mediating mNF-ATx1 nuclear translocation; the amount of mNF-ATx1 translocated with two CN contact points at both CNBR1 and CNBR2 may be greater than the amount elicited by single contact point at CNBR2. The requirement of CNBR2 for the nuclear translocation of mNF-ATx1 may mean that CNBR2 is an essential element for transducing CN-triggered signaling on mNF-ATx1. This idea is supported by the finding that when expressed in Jurkat cells, recombinant CNBR2 suppressed the transcriptional enhancing activity of wild-type mNF-ATx1 (FIG. 8). Compared with CNBR2, it seemed likely that expressed CNBR1 did so to a lesser extent under the same conditions as well as under the conditions in which different amounts of transfected CNBR1 were used (data not shown). Moreover, the level of inhibition of CNBR2 was comparable to that of the whole N-terminal portion of the hNF-ATx molecule.

The mechanism of determination of the intracellular localization of the NF-AT family is a subject to considerable interest. It seems likely that phosphorylation/ dephosphorylation of NF-AT is important for determining intracellular localization; NF-AT resides in the cytoplasm of resting cells in a phosphorylated state (Shibasaki, F. et al., 1996, Nature 382:370; Luo, C. et al., 1996, J. Exp. Med. 184:141; Timmerman, L. A. et al., 1996, Nature 383:837). Upon cell activation, CN dephosphorylates NF-AT directly and, in turn, induces NF-AT nuclear translocation. In this regard, CNBR2 forming a complex with CN probably makes CN accessible to phosphorylated residues, thereby inducing dephosphorylation of these residues, an event essential for the nuclear translocation of NF-AT.

Figure 9:
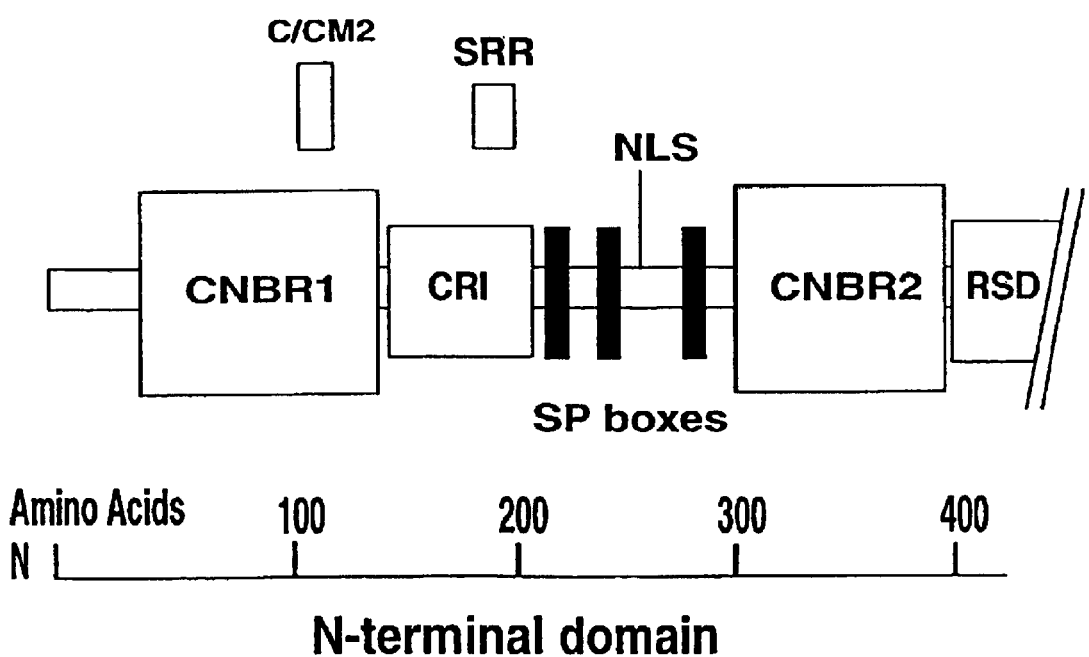
FIG. 9 shows the functional structure of the N-terminal domain of mNF-ATx1. The mNF-ATx1 protein contains two distinct CNBRs (CNBR1 and CNBR2) and other potential motifs that show the sequence conservation to hNF-ATx1 and other family members. C/CM2 of NF-AT4/NF-AT1 (Aramburu, J. et al., 1998, Mol. Cell 1:627; Zhu, J. et al., 1998, Cell 93:851) shown as indicated, overlaps with CNBR1 of mNF-ATx1. The functions of these motifs are discussed below.

It has been reported that an inhibitory sequence of 60 amino acid residues, termed CRI sequence, is located in the region preceding the SP boxes of hNF-ATx1 (FIG. 9). The deletion of this CRI sequence leads to nuclear translocation of hNF-ATx independent of $Ca^{2+}$ signaling (Masuda, E. S. et al., 1997, Mol. Cell. Biol. 17:2066). Likewise, Beals et al. mapped an SRR motif in hNF-ATc with 23 amino acids located within the corresponding CRI region of hNF-ATx (FIG. 9). Mutation of serines in the SRR motif results in nuclear localization of NF-ATc (Beals, C. R. et al., 1997, Genes Dev. 11:824). Therefore, it is reasonable to speculate that the NLS(s) is masked by phosphorylated serine residues in CRI/SRR (Beals, C. R. et al., 1997, Genes Dev. 11:824). mNF-ATx1ΔR1, in which the deletion extends to the CRI/SRR, translocated to the nucleus in a stimulation-dependent manner.

Figure 5:
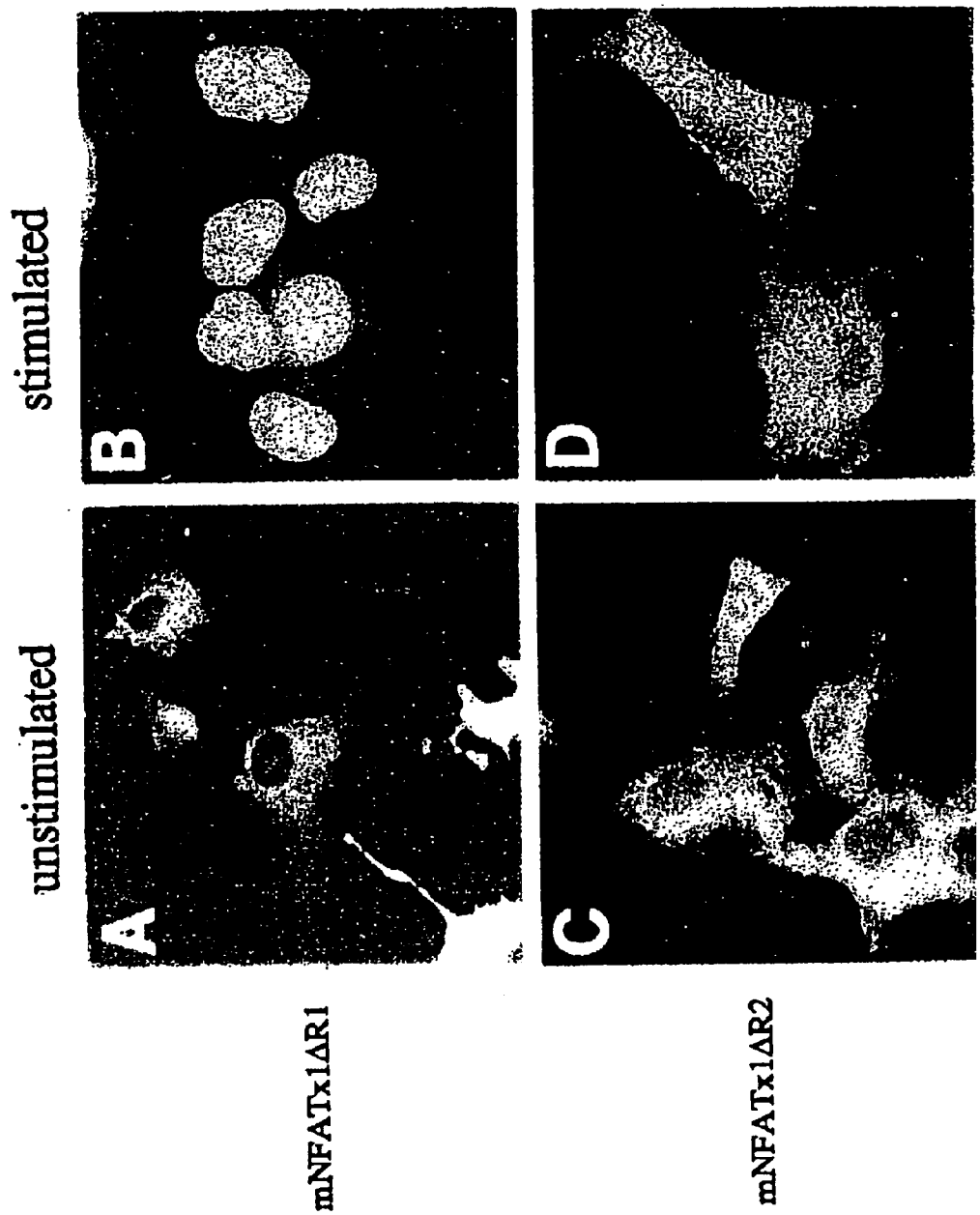
FIG. 5 shows the subcellular localization of mNF-ATx1 deletion mutants. COS-7 cells were cotransfected with 1.25 μg each of pBJ5-CNA and pBJ5-CNB together with 2.5 μg of the expression plasmid pME-mNF-ATx1ΔR1 (A and B) or pME-mNF-ATx1ΔR2 (C and D). The transfected cells were either unstimulated (A and C) or stimulated with 0.5 μM A23187 for 30 min (B and D). Immunostaining was performed using an affinity-purified polyclonal Ab, APαDS.
Figure 6:
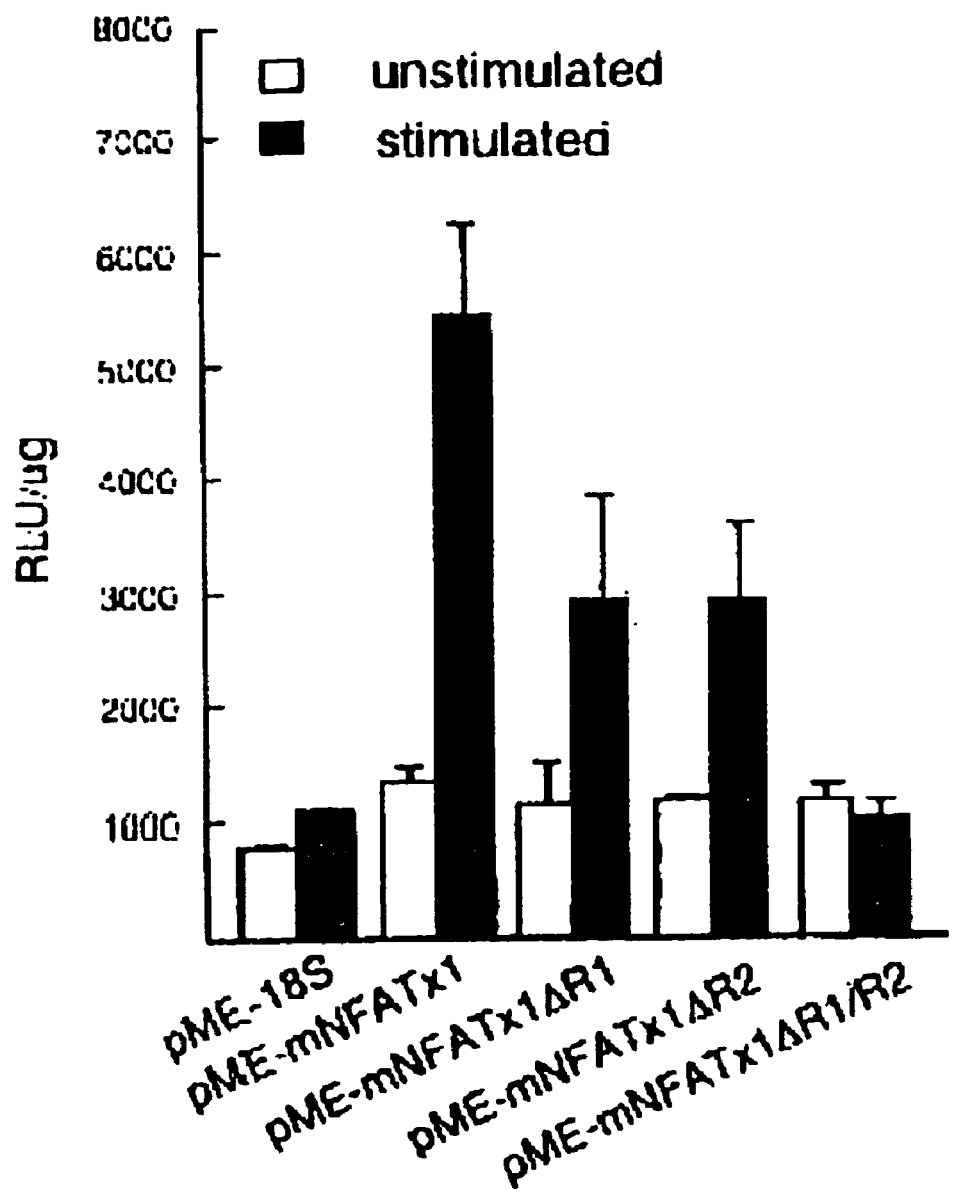
FIG. 6 shows effects of deletion mutations of mNF-ATx1 on transactivation of the IL-2 promoter. COS-7 cells were cotransfected with pmoIL-2-321Luc and pBJ5-CNA plus pBJ5-CNB along with the indicated expression plasmids. The transfected cells either were not stimulated or were stimulated for 8 h with PMA/A23187 as described in EXAMPLES. The relative luciferase unit (RLU) was normalized to the protein concentration by the bicinchoninic acid Protein Assay Reagent (Pierce, Rockford, Ill.). Data shown here are data derived from three independent transfection experiments.

Transcriptional activation of IL-2 promoter mediated by mNF-ATx1 increased markedly in PMA/A23187-stimulated COS-7 cells, when coexpressed with CNA and CNB. However, the transcriptional activity of mNF-ATx1 was reduced after either R1 or R2 was removed from mNF-ATx1 (FIG. 6). The reduction in transactivation activity of mNF-ATx1ΔR1 is probably due to the lack of the N-terminal transactivation domain. (TAD) by deletion of the R1 region. Detailed analysis of the N-terminal TAD has been reported in the case of NF-AT1, in which the TAD was mapped within the first 100 amino acids (Luo, C. et al., 1996, J. Exp. Med. 184:141). In hNF-ATx, TAD is localized within the first N-terminal 400 amino acids. Alternatively, the R1 binding site for CN has no functional significance. The remaining transactivation activity of mNF-ATx1ΔR1 is probably stimulated by translocated mNF-ATx1ΔR1, together with another TAD, which has been mapped at the C-terminus of hNF-ATx1 sharing sequence conservation with mNF-ATx1 (Imamura, R. et al., 1998, J. Immunol. 161:3455). Similarly, PMA/A23187-induced transcription activity of mNF-ATx1 lacking R2 was reduced; however, this was due to impaired nuclear entry (FIGS. 5 and 6), although a low level of translocated molecules may have contributed to the activity to some extent. In fact, when both of two CNBRs were deleted, PMA1A23187-induced transcription activity of mNF-ATx1 was abolished, indicating that full interaction with CN is required for the activation of mNF-ATx1. Taken together, both R1 and R2 deletions caused the reduction of transactivation activity mediated by mNF-ATx1, however, probably through different mechanisms; R1, including a putative transactivation domain, is important for transcriptional activity of mNF-ATx1, while R2 plays an active role in nuclear localization of mNF-ATx1.

In the signal transduction pathway, docking interactions are commonly used for facilitating enzymatic reactions, and the initial docking reaction is probably of higher affinity (Kallunki, T. et al., 1996, Cell 87:929; Stahl, N. et al., 1995, Science 267:1349; Leevers, S. J. et al., 1994, Nature 369:411). It is possible that CNBR2 may function as a docking site, increasing the local concentration of CN next to CNBR1 and directing CN to the phosphorylated residues, thus facilitating mNF-ATx1 dephosphorylation. The lack of well-conserved amino acid sequences between CNBR1 and CNBR2 suggests a model in which two CNBRs interact with a single CN molecule, and each region makes different contact with the same CN. If so, the effects of two CNBRs on CN-mediated signaling to mNF-ATx1 may not be the same. other possibilities including that a secondary or tertiary structure of CNBR1 and CNBR2 may be involved in recognition by CN.

A functional nuclear export signal (NES) has been reported to exist within the corresponding region of CNBR2 in NF-ATc (Klemm, J. D. et al., 1997, Curr. Biol. 7:638). The sequence of the NES is not well conserved among the NF-AT family members, but the leucine-rich sequences, which characterize the NES motif, are found in CNBR2 of mNF-ATx1, suggesting that CNBR2 may contain the NES sequence in mNF-ATx1. Therefore, CN, via the interaction with CNBR2, probably masks the NES and protects it from being recognized by NES receptor(s) during the import process of mNF-ATx1.

CsA and FK506 are potent immunosuppressive agents that block T cell activation and lymphokine production, although other targets of action are also likely to exist (Fruman, D. A. et al., 1992, Eur. J. Immunol. 22:2513; Urdahl, K. B. et al., 1992, Int. Immunol. 4:1341; Shi, Y. F. et al., 1989, Nature 339:625; Bierer, B. E. et al., 1990, Science 250:556). Their serious side effects, including neurotoxicity and nephrotoxicity, have occurred in patients following systemic administration of CsA or FK506, probably related to their molecular target of CN (Dumont, F. J. et al., 1992, J. Exp. Med. 176:751). Other approaches to modulating the immune response with minimal side effects may include developing inhibitor(s) specifically interfering with the interaction between NF-AT and CN. The invention may provide a useful information for developing a new category of immunosuppressants.

Another outcome presented here is that expressed CNBR2 suppressed the reporter gene that was transactivated by the endogenous NF-AT. However, the inhibitory extent was less than its negative effect on the reporter gene that was enhanced by mNF-ATx1 (FIG. 8). It has been demonstrated that although all NF-AT members can bind to the promoters of IL-2 and IL-4, NF-AT1 and NF-ATc account for the majority of the binding activity (Rao, A. et al., 1997, Annu. Rev Immunol. 15:707). Thus, expressed CNBR2 might act as a specific inhibitor of NF-ATx. This was further supported by the fact that the sequences within the corresponding region of CNBR2 among the different family members are not well conserved. The invention shed light on an approach to identifying the unique function of each NF-AT family member.

Although NF-ATR family gene knocked out mice considerably differ in their phenotypes from each other, no difference in the functions of NF-AT members has been observed in vitro experiments (Yoshida, H. et al., 1998, Immunity 8: 115–24; Ranger, A. M. et al., 1998, Immunity 8: 125–34; Xanthoudakis, S. et al., 1996, Science 272: 892–5; Hodge, M. R. et al., 1996, Immunity 4: 397–405; Kiani, A. et al., 1997, immunity 7: 849–60; Oukka, M. et al., 1998, Immunity 9: 295–304; Ranger, A. M. et al., 2000, J. Exp. Med. 191: 9–22; Ranger, A. M. et al., 1998, Immunity 9: 627–35; de la Pompa, J. L. et al., 1998, Nature 392: 182–6). As described above, since CNBR2 is expected to specifically inhibit the activation of NF-ATx family, but not the activation of NF-AT1, etc., the role of NF-ATx can be examined by specifically inhibiting NF-ATx without affecting NF-AT1, etc. using CNBR2 polypeptide under particular circumstances (for example, T cell, helper T cell subsets in vivo, etc.). Considering that CNBR2 polypeptide can exclusively inhibit NF-ATx without affecting the NF-AT1 activity, the polypeptide can be a substitute of CsA as an immunosuppressant with little side effect.

As described below, NF-AT3 has been particularly known of its activity to cause hypertrophy of smooth muscle. Since the CNBR2 regions in NF-AT3 and NF-AF are relatively well conserved, interaction between NF-AT3 and CN may be inhibited by CNBR2 polypeptide. Therefore, CNBR2 expectedly inhibits hypercardia and hypertrophy of vascular smooth muscle associated with hypertension.

Abbreviations

Abbreviations used herein: CN, Calcineurin; CNA and CNB, subunits of wild-type Calcineurin; CsA, cyclosporin A; NF-AT, nuclear factor of activated T cells; AP1, activating protein-1; RSD, Rel similarity domain; NLS, nuclear localization signal; CRI, Calcineurin-regulated inhibitory; SRR, serine-rich region; h, human; m, murine; GST, glutathione S-transferase; CNBR, Calcineurin-binding region; TAD, transactivation domain; NES, nuclear export signal.

Definitions

The following definitions are provided to facilitate understanding of certain terms used frequently herein.

"NF-AT polypeptide" used herein means a general name of NF-AT family proteins. Nuclear factor of activated T-cells (NF-AT) was identified as a protein involved in the expression of cytokine IL-2. Cloning and characterization of NF-AT gene are described in Masuda, E. S. et al., 1995, Mol. Cell. Biol. 15: 2697–706; Ho, S. N. et al., 1995, J. Biol. Chem. 270: 19898–907; Hoey, T. et al., 1995, Immunity 2: 461–72; Luo, C. E. et al., 1996, Mol. Cell. Biol. 16: 3955–66; Northrop, J. P. et al., 1994, Nature 369: 497–502. Five members of NF-AT family proteins are known, and nomenclature of them is shown in the table below.

TABLE 1

| Current Approved Symbol | Another symbol | Literature Aliases | Sequence accessions | Reference PMID |
|---|---|---|---|---|
| NFATC1 | NFAT2 | NFAT2, NF-ATC, NFATc | U08015 | 9506523, 8202141 |
| NFATC2 | NFAT1 | NFAT1, NF-ATP, NFATp | U43341/2 | 7842733, 8668213 |
| NFATC3 | NFAT4 | NFAT4, NFATX | L41067, U14510 | 7749981, 7650004, 7739550 |
| NFATC4 NFATC5 | NFAT3 | NFAT3 | L41066 | 7749981 |
| NFAT5 | NFAT5 | TonE-BP, KIAA0827 | AF089824 AB020634 AF134870 | 10051678 10377394 |

NF-AT polypeptide is usually a Rel protein comprising the Rel similarity domain, and its activation is regulated by calcium. Nuclear transport of this polypeptide is generally inhibited by cyclosporin A (CsA), resulting in the inhibition of its activation. NF-AT polypeptide used in this invention includes not only wild-type NF-AT polypeptides but also fragments thereof, modified NF-AT polypeptides, analogues thereof, etc.

"INF-ATx polypeptide" used herein means one of the NF-AT family members, an NF-AT polypeptide which is highly expressed in thymus (Masuda, E. S. et al., 1995, Mol. Cell. Biol. 15: 2697–706; Liu, J. et al., 1997, Mol. Biol. Cell. 8: 157). The NF-ATx polypeptide includes NF-AT4 polypeptide and NF-ATc3 polypeptide.

"NF-ATx1 polypeptide" used herein means one isoform among NF-ATx. "mNF-ATx1 polypeptide" means a mouse NF-ATx1 polypeptide, and is encoded by the mNF-ATx1 cDNA set forth in Accession Number D85612 (Liu, J. et al., 1997, Mol. Biol. Cell. 8: 157). "hNF-ATx1 polypeptide" means a human NF-ATx1 polypeptide, and is encoded by the hNF-ATx1 cDNA set forth in Accession Number U14510 (Masuda, E. S. et al., 1995, Mol. Cell, Biol. 15: 2697–706).

"Calcineurin (CN)" is generally known as a calcium/calmodulin-dependent serine/threonine phosphatase, existing as a heterodimeric protein composed of a calmodulin-binding catalytic subunit (CNA) and a $Ca^{2+}$-binding regulatory subunit (CNB) (Clipstone, N. A. and Crabtree, G. R., 1992, Nature 357 (6380): 695–7; Tsuboi, A. et al., 1994, Mol. Cell. Biol. 5: 119–28). CN is a target of CsA and FK506, regulating the activation of NF-AT. In this invention Calcineurin (CN) includes not only a heterodimeric protein but also CNA alone or CNB alone and derivatives thereof.

"Polypeptides" used herein mean peptides or proteins comprising two or more amino acid residues linked by peptide bond or modified peptide bond. Polypeptides may include peptide isosteres. Polypeptides usually include short-chain molecules such as those known as peptides, oligopeptides, or oligomers, and also long-chain molecules known as proteins. Polypeptides may be spontaneously modified by post-translational modification, or artificially modified in their peptide backbone, amino acid side chain, amino or carboxyl termini, etc. Polypeptides may be branched by ubiquitination, etc. or cyclized. Examples of modifications include acetylation, acylation, ADP-ribosylation, amidation, covalent attachment of flavin, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of pyroglutamate, formylation, gamma-carboxylation, glycosylation, hydroxylation, iodination, methylation, myristoylation, oxidation, phosphorylation, ubiquitination, etc.

Polypeptides of the Invention

Polypeptides of this invention include a polypeptide set forth in SEQ ID NO: 1 or SEQ ID NO: 2. Both of these polypeptides have the binding activity to Calcineurin (CN). Polypeptides comprising amino acid sequence set forth in SEQ ID NO: 1 or SEQ ID NO: 2 in which one or more amino acids are added, deleted, substituted, and/or inserted are also included in the polypeptides of this invention as far as they maintain the binding activity to CN. Such polypeptides include, for example, a partial polypeptide derived from mNF-ATx1 which shares an overlapping region with SEQ ID NO: 1 or SEQ ID NO: 2 but is not identical with these sequence. For example, SEQ ID NO: 1 is a partial polypeptide consisting of amino acids 25 to 143 of mNF-ATx1 (AC. No. D85612; Liu, J. et al., 1997, Mol. Biol. Cell. 8: 157), but the same polypeptides whose amino terminus is not position 25 but the other position on the amino or carboxyl terminal side from position 25 is included in the polypeptide of this invention, and the polypeptides whose carboxyl terminus is not exactly at position 143 likewise. SEQ ID NO: 2 is a partial polypeptide comprising amino acids 321 to 406 of mNF-ATx1. The polypeptides of this invention include the same polypeptides whose amino or carboxyl termini is not positions 321 or 406 but at other positions on the amino or carboxyl terminal side from positions 321 or 406. Thus, amino and carboxyl termini can be any positions in the amino acid sequence of mNF-ATx1.

Figure 11:
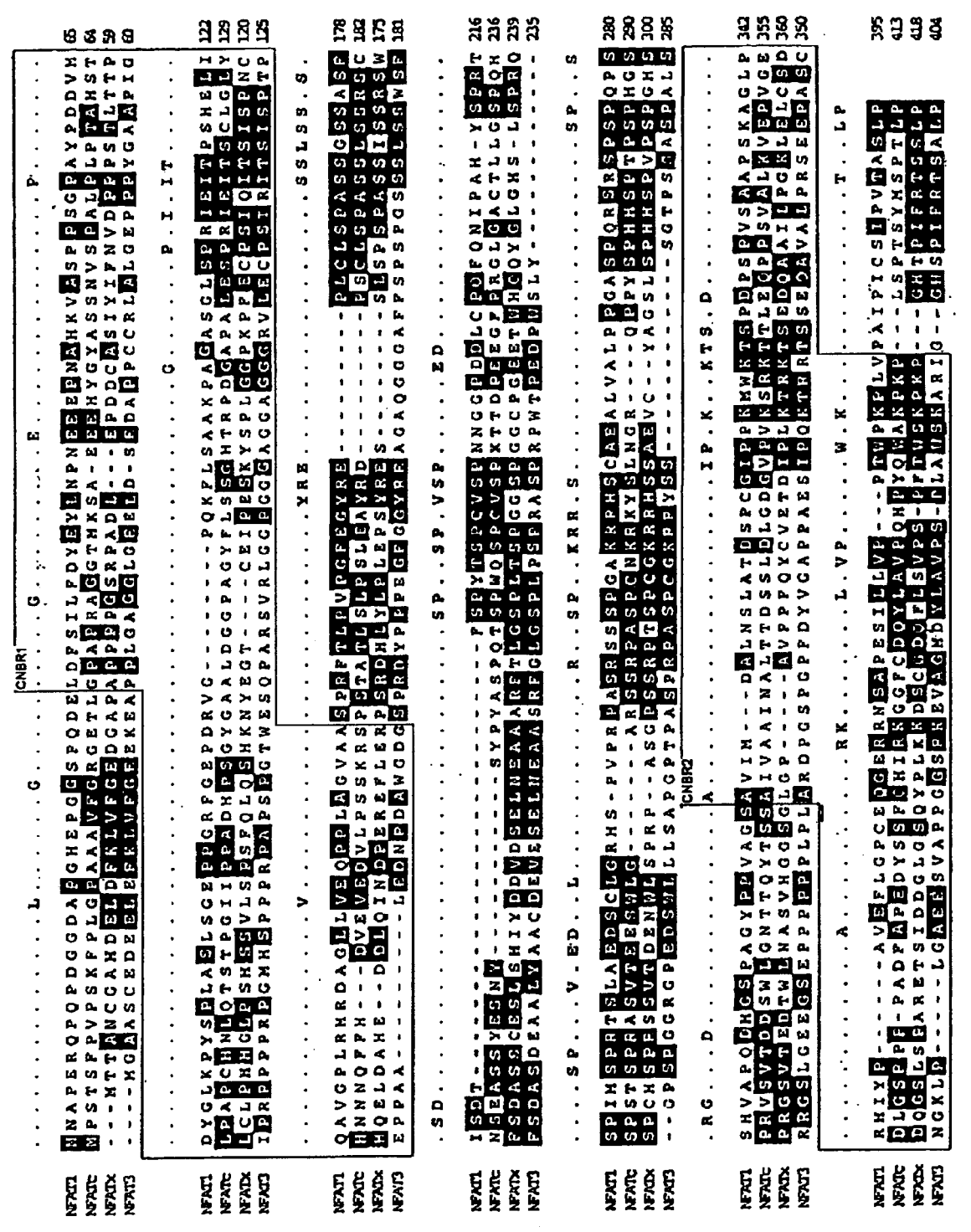

Polypeptides of this invention also include partial polypeptides of the polypeptide encoded by human NF-ATx1 gene (Ac. No. U14510; Masuda, E. S. et al., 1995, Mol. Cell. Biol. 15: 2697–706), comprising regions corresponding to the above-described polypeptides. A polypeptide in a region of a protein "corresponding to" a polypeptide in a region of another protein means a polypeptide at the region shared by both proteins found when both amino acid sequences are aligned. Alignment of amino acid sequences can be performed by Clastal W Alignment using, for example, a "Mac Vector" software (Oxford Molecular). Alignment of N-terminal amino acid sequences of NF-AT family polypeptides are shown in FIGS. 10 and 11 (Masuda, E. S. et al., 1995, Mol. Cell Biol. 15: 2697). More specifically, in the human NF-ATx1 polypeptide (Ac. No. AAA86308), for example, the regions corresponding to CNBR1 (SEQ ID NO: 1) and CNBR2 (SEQ ID NO: 2) of mNF-ATx1 are amino acids 25 to 143 and 321 to 406, respectively. These amino acid sequences are shown in SEQ ID NOs: 3 and 4. Polypeptides of this invention may be derived from regions corresponding to the above-described polypeptides in other NF-AT family proteins.

Polypeptides of this invention can be isolated using hybridization techniques or gene amplification techniques. It is a routine for those skilled in the art to obtain DNA encoding a polypeptide of this invention from DNAs highly homologous to the DNA sequence encoding the mNF-ATx1 protein or a portion thereof isolated from DNA samples derived from organisms of the same or different species using hybridization techniques (Ausubel, F. M. et al., Eds. (1992) Current Protocols in Molecular Biology, 2.9, Green Publishing Associates and Wiley-Interscience, JOHN WILEY & SONS, NY). Conditions for hybridization can be suitably determined. Thus, it is possible to isolate DNA encoding the mNF-ATx1 protein or its structural analogues by hybridization and determine the region of polypeptides of this invention in the isolated DNA. Animals used for isolating such proteins include, for example, rabbits, chicken, pigs, cattle, etc. besides primates such as humans and monkeys, and rodents such as rats and mice, but are not limited thereto. The region corresponding to polypeptides of this invention in proteins other than mNF-ATx1 protein can be selected by aligning amino acid sequences of other proteins with that of mNF-ATx1 protein and determining the regions in the amino acid sequences corresponding to a polypeptide of this invention that is the partial polypeptide of mNF-ATx1 protein. Once the region is determined, a recombinant protein can be prepared by appropriately inserting the DNA region encoding the partial polypeptide into an expression vector.

It is also possible to prepare polypeptides of this invention by amplifying DNAs encoding mNF-ATx1 protein, its structural analogues, or portions thereof using polymerase chain reaction (PCR) (Ausubel, F. M. et al., Eds. (1992) Current Protocols in Molecular Biology, 15, Green Publishing Associates and Wiley-Interscience, JOHN WILEY & SONS, NY).

The amino acid sequences of polypeptides of this invention including partial polypeptides of wild-type mNF-ATx1 proteins, may have mutations as long as they have the binding activity to, CN. Such mutations may be introduced spontaneously or artificially. In the case of artificial amino acid substitution, the activity of the intact polypeptide can be maintained by substituting amino acid(s) with the one(s) of similar property. Polypeptides of this invention include the partial polypeptides of the wild-type protein modified by the conservative amino acid substitution.

A "conservative amino acid substitution" is one in which the amino acid residue is replaced with another residue having a chemically similar side chain. Families of amino acid residues having similar side chains have been defined in the art. These families include amino acids with basic side chains (e.g., lysine, arginie, histidine), acidic side chains (e.g., aspartic acid, glutamic acid), uncharged polar side chains (e.g., glycine, aspargine, glutamine, serine, threonine, tyrosine, cysteine), nonpolar side chains (e.g., alanine, valine, leucine, isoleucine, proline, phenylalanine, methionine, tryptophan), beta-breached side chains (e.g., threonine, valine, isoleucine) and aromatic side chains (e.g., tyrosine, phenylalanine, tryptophan, histidine). It is also possible to isolate a polypeptide with a stronger binding activity to CN by varying amino acids of polypeptides at random and screening those variants.

In polypeptides of this invention with mutations in amino acid sequence of the partial polypeptide of the wild-type protein (e.g. SEQ ID NO: 1 or SEQ ID NO: 2), the number of amino acid that can added, deleted, substituted, and/or inserted in usually 50 or less, preferably 30 or less, more preferably 15 or less, and still more preferably 10 or less.

A polypeptide of this invention may be a fusion polypeptide with other polypeptide species. A "fusion polypeptide with other polypeptide species" used herein means a polypeptide produced by linking at least two polypeptides that are not joined in nature, and can be produced by expressing a nucleic acid comprising the coding regions of the polypeptides linked so as to be in frame. Other polypeptide species includes tag sequence, GPP, maltose-binding protein, glutathione S-transferase (GST), etc., but are not limited thereto.

The binding activity to CN can be assessed by known techniques such as pull-down assay, immunoprecipitation, ELISA, Two hybrid system, BIACORE, etc. Although the wild-type CN is composed of plural subunits (subunits A and B), for example, CNA or ΔCNA lacking the regulatory region (constitutive active CNA) can be used in the binding assay to NF-AT. However, since the co-existence of CNB with CNA confers a high binding capacity on CN both subunits of CN are preferably used in the assay. CN used in the assay can be either the one expressed in *Esoheriohia coli* or the one purified or partially purified from tissues abundant in CN such an brain, etc.

For example, a desired polypeptide in expressed as a fusion polypeptide with GST. Cell lysates which express CN (CNA and CNB) are incubated with glutathione-Sepharose 4B-bound GT-fusion protein in buffer containing 150 mM NaCl, 50 mM HEPES buffer, 10 μM $CaCl_2$, 0.25 Nonidet P-40, and protease inhibitors. After washing the beads, the glutathione-Sepharose 4B-found fraction is eluted by boiling in gel loading buffer and analyzed by SDS-PAGE. Bound proteins can be visualized using anti-CNR and anti-GST mAbs.

By these assays, it is also possible to isolate a polypeptide. of minimum length retaining CR-binding capability and a mutant polypeptide with a stronger CN-binding activity.

Polypeptides of this invention can be prepared by purifying the wild-type polypeptide, or prepared as recombinant polypeptides using recombinant technology well known to those skilled in the art. The polypeptides may also be synthesized. A recombinant polypeptide can be prepared, as described below, for example, by transfecting suitable host cells with a vector into which DNA encoding the polypeptide of this invention is inserted and recovering the polypeptide expressed in the transformant.

DNA of the Invention

The present invention also relates to DNAs encoding polypeptides of this invention. There is no particular limitation in the type of these DNAs as long an they can encode polypeptides of this invention, including cDNA, genomic DNA, chemically synthesized DNA, etc. DNAs comprising nucleotide sequences based on the degeneracy of genetic code are also included as long as they can encode polypeptides of this invention. DNAs set forth in SEQ ID NO: 1 or 2 can be isolated by, for example, standard method such as hybridization using the DNA sequence encoding mNF-ATx1 protein (Ac. No. D85612; Liu, J. et al., 1997, Mol. Biol. Cell. 8: 157) or a portion thereof as the probe, PCR using primers synthesized based on these DNA sequences, etc. These DNAs can also be synthesized with a DNA synthesizer.

DNAs of this invention can be used to produce polypeptides of this invention as recombinant proteins by inserting the DNA into the vector as described below, and introducing the vector into host cells. As described above, a fusion polypeptide with other polypeptide species can be produced by connecting the coding region of the polypeptide of this invention with that of the other polypeptide species so as to be in frame. Other polypeptide species include leader sequence, secretion signal, and sequence of pre- or pro-sequence. Addition of tag sequence can facilitate the purification of polypeptides. Examples of the tag sequence include 6×His, HA tag, etc. DNAs of this invention can be modified so that they can encode fusion proteins with other proteins such as GFP, maltose-binding protein, glutathione S-transferase (GST), etc. DNAs of this invention may comprise, in addition to coding regions, non-coding sequences (non-transcriptional sequence, non-translational sequence, splicing sequence, poly A addition sequence, IRES, mRNA stabilization/destabilization sequence, etc.).

Vectors, Transformants, Expression

The present invention also provides vectors carrying DNAs of this invention. There is no particular limitation in the type of vectors of this invention as long as they can stably retain inserted DNAs. Vectors of this invention include plasmids, phonemics, phages, cosmos, chromosomes, viruses, etc. The type of host cells is not particularly limited, and includes, for example, *Escherichia coli*, yeasts, plant cells, animal cells, etc. Preferable animal cells are, for example, insect cells and mammalian cells. Individuals of animals and plants can also be used as hosts.

Polypeptides of this invention can be prepared in a large scale, by, for example, using the *Escherichia coli* expression system. The polypeptides can be expressed using well-known expression vectors such as pGMEX (Promega), etc. The expressed polypeptides can be secreted into the endoplasmic reticulum, periplasm, or outside of cells if secretion signal is suitably attached to the polypeptides. The extracellularly secreted polypeptides can be purified from the culture medium of the transformants. When the polypeptides are intracellularly expressed, the transformants are collected and lysed to recover the polypeptides. The polypeptides can be prepared by known protein purification methods such as ammonium sulfate precipitation, cationic or anionic exchange chromatography, gel filtration, affinity chromatography, HPLC, etc. Vectors can be introduced into host cells by the calcium chloride method, electroporation method, etc.

Vectors to be used for transfection of mammalian cells, include, for example, pME18s vector, etc. Cell lines into which the vectors are introduced include, for example, COS cells, CHO cells, 3T3 cells, BHK cells, 293 cells, etc. Host cells may not be necessarily the established cell line. For example, primary cultures, *Xenopus laevis* oocytes, etc. may be used. Vectors can be introduced into host cells by the calcium phosphate method, DEAE-dextran method, electroporation method, lipofection method, injection method, etc. (Ausubel, F. M. et al., Eds. (1992) Current Protocols in Molecular Biology, New York: Green Publishing Associates and Wiley-Interscience).

The vectors of this invention to be used for gene therapy are preferably virus vectors. The virus vectors include, for example, known vectors such as retrovirus vectors, adenovirus vectors, adeno-associated virus vectors, etc. (Kurata, H. (1999) Immunity 11: 677–88; Robbins, P. D. (1998) Trends Biotechnol. 16: 35–40). For gene therapy, for example, the DNA of this invention is inserted into the vector, and the vector is administered to living bodies. Vectors may be administered either in vivo or ex vivo.

Screening Assays

This invention also provides a method for screening a compound that inhibits the interaction between CN and NF-AT using the polypeptide of this invention. CN dephosphorylates NF-AT to convert it into an active form and induces its transport into nuclei. Therefore, the inhibition of interaction between CN and NF-AT will block signal transduction from CN to NF-AT.

The screening method of the present invention comprises: (a) contacting the polypeptide of this invention with Calcineurin in the presence or absence of a sample; (b) detecting the binding activity of the polypeptide to Calcineurin; and (c) selecting a compound that reduces the binding activity compared to the binding activity detected in the absence of a sample.

The sample to be used in the above method includes, for example, supernatants from culture medium of microorganisms, natural ingredients derived from plants or marine organisms, biological tissue extracts, cell extracts, expression products of a gene library, synthetic low molecular weight compounds, synthetic peptides, natural compounds, etc., but are not limited thereto. Peptides that strongly inhibit the binding between the polypeptide of this invention and CN can be isolated by, for example, screening a random peptide library.

The polypeptide of this invention as it is or a mutant polypeptide thereof can be used as the sample. As shown in FIG. 8, for example, the CNBR2 polypeptide of mNF-ATx1 expresses by itself a dominant negative phenotype against the binding of NF-AT to CN. Therefore, a minimum polypeptide unit in the amino acid sequence of CNBR2 polypeptide necessary for inhibiting the binding of NF-AT to CN can be identified by the screening assay of this invention using a partial peptide of the CNBR2 polypeptide as a sample taking the binding inhibition between the polypeptide of this invention and CN as an index.

The polypeptide of this invention used for screening may be, for example, in the form expressed on the cell surface: a cell membrane fraction of the cells. or the form bound to a carrier. CN to be used is, for example, CNA or ΔCNA lacking the regulatory domain (constitutive active CNA).

Herein. the co-existence of CNB and CNA is preferable because It enhances the binding capacity to the polypeptides of this invention. CN can be the one expressed in *Escherichia coli* or the one purified or partially purified from tissues abundant in CN such as brain, etc.

The binding activity of the polypeptides of this invention to CN can be assessed, as described above, by well-known methods such an pull-down assay, immunoprecipitation, ELISA, two hybrid system, BIACORE, etc.

More specifically, CNA or ΔCNA expressed in *Escherichia coli*, etc. is adsorbed onto a plastic support (for example, 96-well plate, etc.). In this case, CNA is preferably used together with CNB. In the presence of a test compound, a compound that inhibits the interaction between CN and the polypeptide of this invention is selected by adding the biotinylated polypeptide of this invention to the reaction system, and detecting the polypeptide bound to CN using avidin-bound antibody or avidin-bound fluorescence reagent, etc.

A method utilizing surface plasmon resonance, high through put screening method in combinatorial chemistry technique, etc. can also be used.

Compounds capable of reducing the binding activity of the polypeptide of this invention to CN obtained by this screening method can be used to develop novel drugs. Herein, "reducing the binding activity of the polypeptide of this invention to CN" means reducing the binding activity of the polypeptides of this invention to CN by either directly or indirectly acting on the polypeptide of this invention or CN. Therefore, compounds isolated by this screening method include not only compounds that reduces the binding of the polypeptide of this invention to CN by directly acting on either one of them but also compounds that reduce the binding activity without directly interfering with their binding itself.

The polypeptides, DNAs, vectors of the present invention, and compounds isolable by the screening method of this invention are useful for inhibiting the interaction between CN and NF-AT. The interaction between CN and NF-AT is inhibited in cells by introducing one or more polypeptides of the present invention or compounds isolable by the screening method of this invention into the cells, or by expressing either the DNAs or vectors of this invention in the cells, thereby blocking signal transduction from CN.

Pharmaceutical Compositions and Administration

The polypeptides of this invention or compounds isolable by the screening method of the invention can be administered to patients, for example, in a dose pharmaceutically effective to sufficiently inhibit the interaction between CN and NF-AT. The polypeptides of this invention may be modified ones or their derivatives. Modification or derivatization of polypeptides can lead to the improvement of their stability or cell permeability in vivo. The polypeptides of this invention may be in the form of salts thereof. The polypeptides in these forms can be administered, for example, intravenously or orally. The polypeptides of this invention or compounds isolable by the screening method of the invention can be administered in suitable combinations with pharmaceutically acceptable carriers. In addition, the DNAs or vectors of this invention can be administered in an amount to express and produce the polypeptides sufficient to inhibit the interaction between CN and NF-AT. The DNAs of this invention can be incorporated into retrovirus vectors, adenovirus vectors, etc. and introduced into patient cells in vivo or ex vivo.

The polypeptides of this invention or compounds isolable by the screening method of the invention are useful as novel immunosuppresants with less side effects than conventional drugs. In addition, NF-AT is reportedly involved in hypertrophy of smooth muscle and skeletal muscle (Boss, V. et al., 1998, J. Biol. Chem. 273: 19664–71; Abbott, K. L. et al., 1998, Mol. Biol. Cell. 9: 2905–16; Wang, X. G. et al., 1997, Mol. Pharmacol. 52:781–7; Musaro, A. et al., 1999, Nature 400: 581–5; Semsarian, C. et al., 1999, Nature 400: 576–81; Molkentin, J. D. et al., 1998, Cell 93: 215–28; Izumo, S. and H. Aoki, 1998, Nat. Med. 4: 661–2). The fact indicates that hypercardia and hypertrophy of the vascular wall can be prevented by inhibiting the activation of NF-AT in smooth muscle and/or skeletal muscle.

When the polypeptides of this invention or compounds isolable by the screening method of the invention are used as the drug, these can be administered to patients either as they are or as pharmaceutical compositions formulated by known pharmaceutical methods. The polypeptides or the compounds may be formulated, for example, together with pharmaceutically acceptable carriers or media, such as sterilized water, physiological saline, dextrose, glycerol, ethanol, vegetable oil, emulsifier, suspending agent, etc. The pharmaceutical compositions of this invention may be in the form of an aqueous solution, tablets, capsules, troches, buccal preparations, elixirs, suspensions, syrups, etc. Contents of active ingredients may be appropriately determined. The compositions can be administered to patients in general by known methods such as intra-arterial injection, intravenous injection, intraperitoneal injection, subcutaneous injection, oral administration, etc. Administration can be performed systemically or locally. Doses may vary depending on properties of these polypeptides or compounds, body weight or age of patients, administration method, symptoms, etc., and can suitably be selected by those skilled in the art. Usual doses typically range from about 0.01 mg/kg to 1 g/kg, preferably about 0.05 mg/kg to 100 mg/kg, and more preferably about 0.1 mg/kg to 50 mg/kg per day in a single dose or several divided doses. When the polypeptides or the compounds is encoded by DNA, gene therapy may be performed by incorporating the DNA into a vector for gene therapy and administering the vector ex vivo or in vivo.

The examples below are carried out using standard techniques, which are well known and routine to those of skill in the art, except where otherwise described in detail. These examples are offered by way of example and not by way of limitation. Variations and alternate embodiments will be apparent to those of skill in the art.

EXAMPLE 1

CN Interacts Independently with Two Distinct Regions within the N-terminal Domain of mNF-ATx1

To determine whether the N-terminal domain of mNF-ATx1 could mediate the association with CN, the construct encoding the fusion protein (GST-XND) of the N-terminal domain of mNF-ATx1 (amino acids 25–406) (Liu, J. et al., 1997, Mol. Biol. Cell. 8:157) with GST was made and expressed in *E. coli*. The purified GST-XND fusion protein was used for in vitro CN binding assay. The expression plasmid used for mNF-ATx1 (pME-mNF-ATx1) was previously described (Liu, J. et al., 1997, Mol. Biol. Cell. 8:157). pBJ5-CNA and pBJ5-CNB, which encode CNA and CNB subunits, were provided by N. A. Clipstone and G. Crabtree (Stanford University, Stanford, Calif.) (Clipstone, N. A. and Crabtree, G. R., 1992, Nature 357:695–7; Tsuboi, A. et al., 1994, Mol. Cell. Biol. 5:119–28).

For the CN binding assay, the purified GST-XND fusion protein or GST protein immobilized on glutathione- Sepharose 4B beads, or glutathione-Sepharose 4B alone was incubated with cell lysates isolated from COS-7 cells that had been transfected with the expression vectors for the wild-type CN (pBJ5-CNA and pBJ5-CNB) in buffer containing 150 mM NaCl, 50 mM HEPES buffer, 10 µM $CaCl_2$, 0.25% Nonidet P-40, 1 µg/ml of leupeptin, 1 µg/ml of aprotinin, 10 mM NaF, 1 MM $NaV_3O_4$, and 10 mM Na pyrophosphate. After washing the beads, the glutathione-Sepharose 4B-bound fraction was eluted by boiling in Laemil's sample buffer and analyzed by SDS-PAGE followed by Western blot analysis, using anti-CNA (Sigma) mAbs and anti-GST (Santa Cruz Biotechnology, Santa Cruz, Calif.) mAbs, respectively. As shown in FIG. 1, CN was detected when GST-XND was used (lane 3); however, no CN was observed when glutathione-Sepharose 4B-bound GST or glutathione-Sepharose 4B alone was used under the same conditions (lanes 4 and 5), suggesting that CN binding depended on the presence of the N-terminal domain of mNF-ATx1.

To locate precisely the CN binding portion within the N-terminal domain of mNF-ATx1, a series of GST fusion proteins of mNF-ATx1 mutants having the N-terminal truncations was prepared (FIG. 2A). or a series of GST fusion constructs, DNA fragments derived from the N-terminal domain of mNF-ATx1 were inserted into either pGEX4T-1 or pGEX-5X-3, according to the reading frame (Pharmacia, Piscataway, N.J.). All GST fusion proteins and GST protein expressed in *Escherichia coli* strain BL21DE3 were affinity purified according to the manufacturer s instructions (Pharmacia). The CN binding assay was performed under the same condition as described above. These fusions were analyzed by SDS-PAGE followed by either Coomassie brilliant blue staining (data not shown) or Western blots using an anti-GST Ab (FIG. 3).

XNΔR2 was a deletion mutant lacking the region between the SP boxes and the RSD. Binding assay with GST-XNR fusion protein and COS-expressed CN showed that such deletion had no significant effect on its CN binding activity, compared with that of GST-XND fusion protein (FIG. 3). Likewise, when expressed in *E. coli* as a GST fusion protein, XNΔR1, in which the N-terminal region preceding the SP boxes was removed from XND, still bound to CN (FIG. 3). However, when further deletion was made in XNΔR1 at its C-terminus to yield XNΔR12, the CN binding activity of GST-XNΔR12 was drastically reduced. The lack of CN binding activity of GST-XNΔR12 fusion protein was not due to a lower amount of the protein used. Blotting of the filter by anti-GST Ab revealed that the amount of GST-XNΔR12 fusion protein, which was more than the amount of GST-XND or GST-XNΔR2 fusion, was still comparable to that of GST-XNΔR1 fusion protein (FIG. 3, lower panel).

Taken together, these results showed that both GST-XNΔR1 and GST-XNΔR2 fusion proteins are capable of interacting with CN and that the individual deletion of either R1 or R2 did not abolish the potential of mNF-ATx1 to bind CN. Since GST-XNΔR12, which contains the overlapping region of both GST-XNΔR1 and GST-XNΔR2, failed to bind CN, mNF-ATx1 is likely to contain two CN binding regions (CNBRs): R1, localized at the region preceding the SP boxes, contains the amino acid residues 25–188; R2, corresponding to the region between the SP boxes and RSD of mNF-ATx1, contains the amino acid residues 317–406.

EXAMPLE 2

Removal of the R2 Region Results in Impairment of the Nuclear Translocation of mNF-ATx1

Since the CN binding of mNF-ATx1 seemed to be mediated via either R1 or R2, the inventors next asked whether the subcellular localization of mNF-ATx1 would be affected by deleting R1 and R2. To address this question, the inventors prepared expression constructs of pME-mNF-ATx1ΔR1 and pME-mNF-ATx1ΔR2, in which R1 and R2 were deleted, respectively (FIG. 4). pME-mNF-ATx1ΔR1, pME-mNF-ATx1ΔR2, and pME-mNF-ATx1ΔR1/R2 were obtained from pME-mNF-ATx1 (Liu, J. et al., 1997, Mol. Biol. Cell. 8:157) by deleting the N-terminal region preceding the SP boxes of mNF-ATx1 (nucleotide positions between 79–571, R1), the region between the SP boxes and the RSD (nucleotide positions between 966–1227, R2), and the region covering both R1 and R2 of mNF-ATx1, respectively. As reported previously, in COS-7 cells, nuclear translocation of overexpressed mNF-ATx1 molecule depends on coexpression of the wild-type CN followed by stimulation of the cells with calcium ionophore (Liu, J. et al., 1997, Mol. Biol. Cell. 8:157). Therefore, pBJ5-CMA and pBJ5-CNB were cotransfected with pME-mNF-ATx1ΔR1 or pME-mNF-ATx1ΔR2 into COS-7 cells. mNF-ATx1ΔR1 and mNF-ATx1ΔR2 expressed in COS-7 cells were visualized by immunofluorescence staining as previously described (Liu, J. et al., 1997, Mol. Biol. Cell. 8:157). An affinity-purified polyclonal Ab, APαDS, raised against a bacterially produced recombinant peptide of human NF-ATx (hNF-ATx) extending from amino acid residues 387–728 (Masuda, E. S. et al., 1995, Mol. Cell. Biol. 15:2697), was used to detect mNF-ATx1 and its mutants. This Ab recognizes the RSD of hNF-ATx1. The secondary Ab used was FITC-labeled goat anti-rabbit IgG (Zymed, South San Francisco, Calif.). The immunostaining revealed that mNF-ATx1ΔR1 was present predominantly in the cytoplasm of unstimulated cells (FIG. 5A). Following activation of the cells by A23187, mNF-ATx1ΔR1 translocated to the nucleus of most transfected cells (FIG. 5B). In marked contrast, mNF-ATx1ΔR2 showed no significant redistribution to the nucleus in response to the activation of CN in immunostaining (FIG. 5, C and D); mNF-ATx1ΔR2 remained in the cytoplasm of 90% of transfected cells. Although the accumulation of mNF-ATx1ΔR2 in the nucleus was observed in some activated cells, it represented only a small population among the transfected cells compared with that of mNF-ATx1ΔR1.

These results indicate that R2 is a domain actively involved in the nuclear localization of mNF-ATx1 and is indispensable for this process, whereas R1 elicits less drastic effects and cannot by itself transport mNF-ATx1 to the nucleus.

EXAMPLE 3

Deletion of Either the R1 or R2 Region Abolishes mNF-ATx1-mediated Transcriptional Activation of the Murine IL-2 Gene On the basis of the observation that removal of R2 reduced the nuclear translocation activity of mNF-ATx1, the inventors then examined the roles of R1 and R2 in mNF-ATx1-dependent gene activation. COS-7 cells were grown in DMEM medium containing 10% FCS, 50 U/ml of penicillin, and 50 µg/ml streptomycin. Jurkat cell lines were cultured in RPMI 1640 medium supplemented with 5% FCS, 2 mM L-glutamine, 50 µM 2-ME, 50 U/ml of penicillin, and 50 µg/ml streptomycin. Transfections into COS-7 and Jurkat cells were conducted as previously described (Masuda, E. S. et al., 1997, Mol. Cell. Biol. 17:2066; Liu, J. et al., 1997, Mol. Biol. Cell. 8:157). pNF-AT72Luc containing the luciferase reporter gene under control of three copies of the murine IL-2 distal NF-AT sites (−290 to −261) (Tsuruta, L. et al., 1995, J. Immunol. 154:5255) and pmoIL-2-321Luc containing the luciferase reporter gene under control of the IL-2 promoter that covers the position of −321 to +46 were constructed as previously described (Tsuruta, L. et al., 1995, J. Immunol. 154:5255). pCMV-SEAP (Tropix, Bedford, Mass.), used as an internal control to evaluate transfection efficiency, is an expression vector of secreted alkaline phosphatase.

For luciferase assays performed in COS-7 cells, 6 μg of pmoIL-2-321Luc reporter plasmid and 6 μg of pME-mNF-ATx1, pME-mNF-ATx1ΔR1, pME-mNF-ATx1ΔR2, or pME-mNF-ATx1ΔR1/R2 with pBJ5-CNA plus pBJ5-CNB plasmid were used. pME-18S was used to adjust the total amount of DNA transfected, as required. In competition experiments, Jurkat cells were transfected with 1 μg of pNF-AT72Luc plus 0.5 μg of pCMV-SEAP and either 0.25 μg of pME-mNF-ATx1 or pME-18S alone or together with 0.75 μg of pcDNA-His-CNBR2. The pcDNA3.1/His empty vector was used to adjust the total amount of DNA transfected, as required. Luciferase activity was measured using the Luciferase Assay System (Promega, Madison, Wis.).

As shown in FIG. 6, when expression vectors encoding the wild-type mNF-ATx1 (pME-mNF-ATx1) as well as CMA and CNB were transfected into COS-7 cells, exposure of the cells to PMA/A23187 enhanced transcription activity of the murine IL-2 promoter 4-fold over that of untreated cells. However, when pME-mNF-ATx1ΔR1 or pME-mNF-ATx1ΔR2 was used instead of pME-mNF-ATx1, mNF-ATx1-dependent transcription activity of the exogenous IL-2 promoter was decreased 1.8- or 1.9-fold following stimulation of the cells by PMR/A23187, respectively. Further deletion of both R1 and R2 resulted in the impairment of mNF-ATx1 transcription activity. Thus, both R1 and R2 are apparently essential for mNF-ATx1-dependent IL-2 promoter transcriptional activity.

EXAMPLE 4

CNBR2 of mNF-ATx1 Exhibits Potent CN Binding Activity

Figure 2:
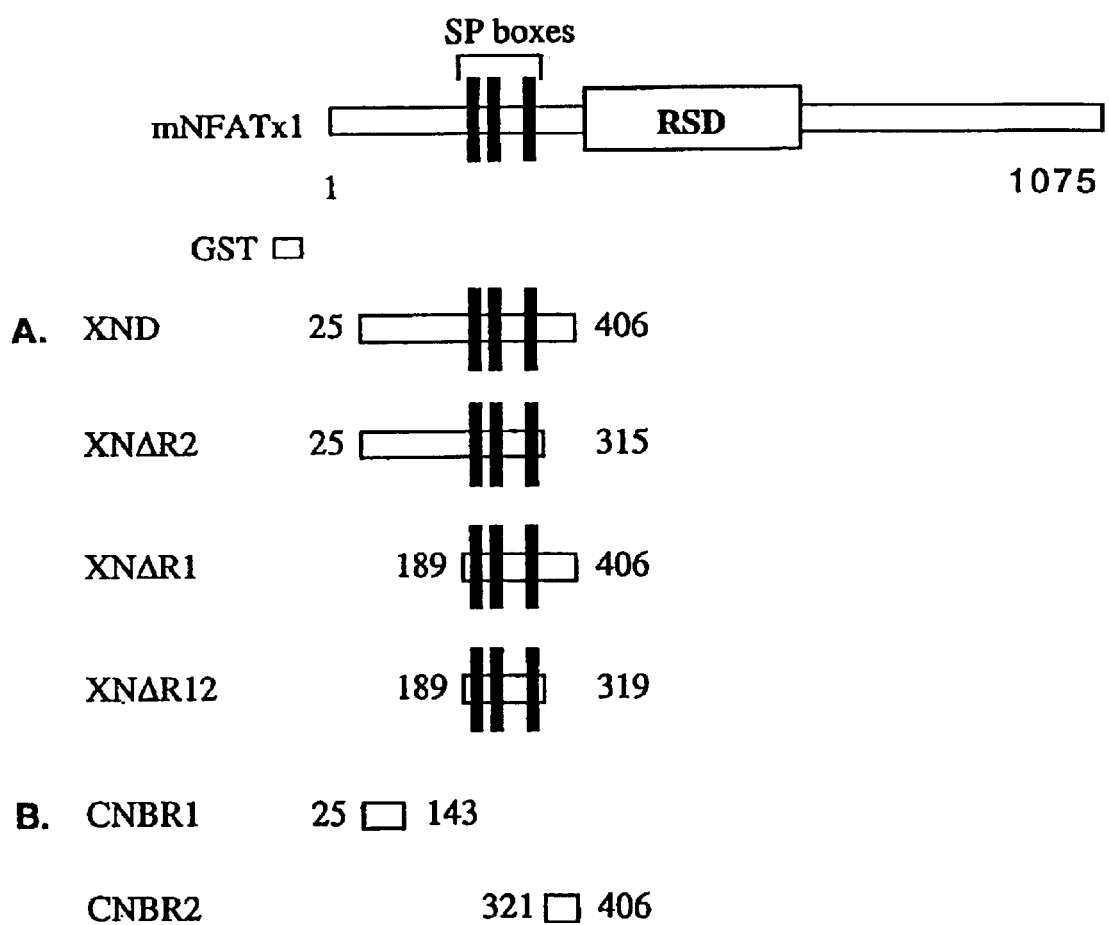
FIG. 2 schematically shows deletion mutants of GST-mNF-ATx1 fusion protein. Numbers indicate amino acid portions in mNF-ATx1 (Liu, J. et al., 1997, Mal. Biol. Cell. 8:157) of different mutants. The SP boxes and the RSD are indicated.
Figure 7:
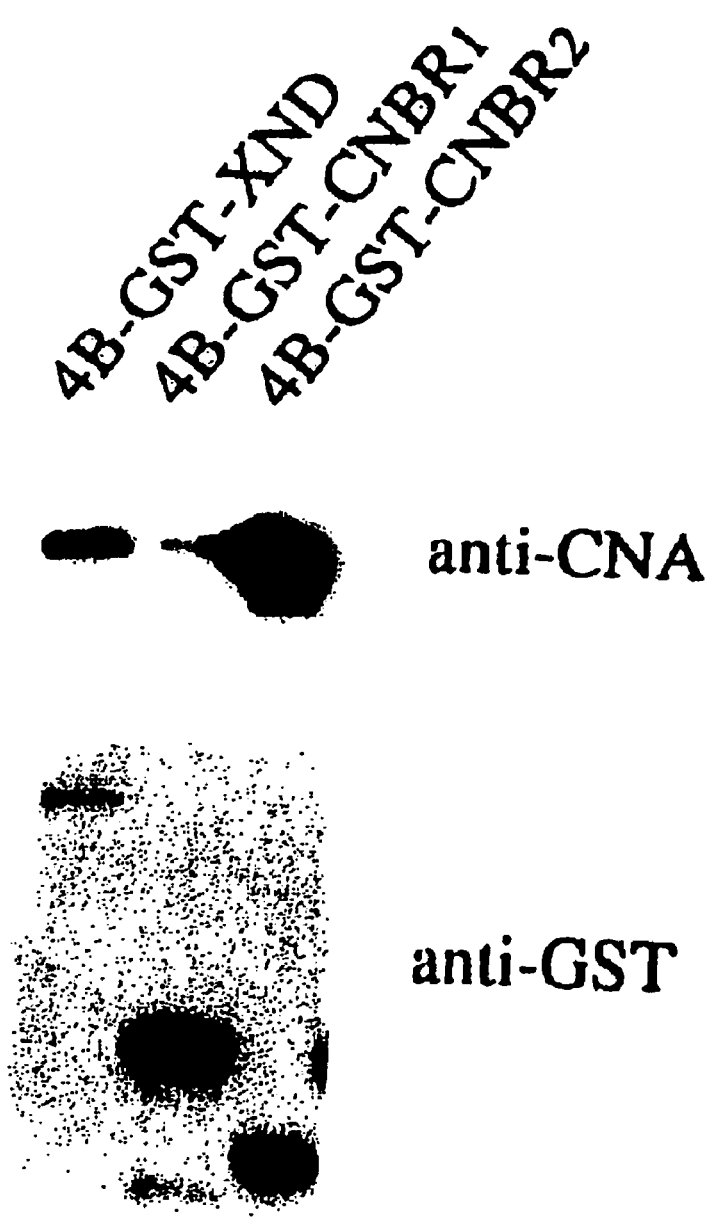
FIG. 7 shows that CN interacts with mNF-ATx1 at two distinct regions. CN binding assays were conducted under the same conditions as those described in FIG. 1, except that glutathione-Sepharose 4B-bound GST-CNBR1 and GST-CNBR2 fusion proteins were used. Glutathione-Sepharose 4B-bound GST-XND was used as a control.

The results described above show that R1 and R2 have different roles in transmitting the CN-mediated signal to mNF-ATx1; i.e., removal of R2 abolished nuclear translocation of mNF-ATx1, but removal of R1 did not, although both are involved in the CN binding event. To clarify why they elucidate the different functions, the inventors next examined the direct interactions of CN with these two regions. CNBR1, including amino acid residues of 25–143, is 45 amino acids shorter than R1; CNBR2, containing amino acid residues of 321–406, covers a region similar to that of R2 (FIG. 2B). Constructs encoding the GST fusion protein of CNBR1 or CNBR2 were expressed in *E. coli*. The purified GST-CNBR1 and GST-CNBR2 proteins were used to perform the binding assay under the same conditions as those described above. As expected, both GST-CNBR1 and GST-CNBR2 fusion proteins bound CN (FIG. 7), while no CN was observed when GST alone was used (data not shown). Remarkably, GST-CNBR2 fusion showed a much stronger CN binding activity than did the GST-CNBR1 fusion protein. This result was further confirmed using different amounts of purified CN, showing that the CN binding of GST-CNBR1 could be enhanced by the addition of increased amounts of purified CN. Nevertheless, its binding activity was weaker compared with that of GST-CNBR2 under the same conditions (data not shown). It suggested that the different functions of two CN binding regions might be due to different CN binding potentials.

EXAMPLE 5

CNBR2 Polypeptide Exerts a Dominant Negative Effect on mNF-ATx1-dependent Transcription Activity Previous study has shown colocalization of CN with NF-AT4 in the nucleus of cells from the U2OS cell line (Shibasaki, F. et al., 1996, Nature 382:370). The inventors also observed that CN migrates to the nucleus together with mNF-ATx, when coexpressed in COS-7 cells that had been stimulated with A23187 (data not shown). Based on the evidence of potent CN binding activity of CNBR2, the inventors hypothesized that recombinant CNBR2 acts in a dominant negative manner by titrating out CN interacting with mNF-ATx1. To test this possibility, CNBR2 cDNA fragment derived from mNF-ATx1 was constructed into the His-tagged expression vector pcDNA3.1/His (Invitrogen, Carlsbad, Calif.) to yield pcDNA-His-CNBR2. As shown in FIG. 8, when Jurkat cells were cotransfected with pNF-AT72Luc and pcDNA3.1/His empty vector, the promoter activity, which was very low in the cells before stimulation, increased following treatment of the cells with PMA/A23187. This activity is probably supported by the action of endogenous NF-AT. When pME-mNF-ATx1 was introduced into the cells, the promoter activity was further enhanced as much as 2.9-fold following stimulation. Interestingly, this enhancement by mNF-ATx1 was suppressed when the cells were transfected with pME-mNF-ATx1 along with pcDNA-His-CNBR2. Interestingly, the inventors also found that expressed CNBR2 elicited an inhibitory effect on the reporter gene that was transactivated by the endogenous NF-AT; however, this effect was much less effective compared with that of mNF-ATx1-dependent reporter gene activity. Therefore, as predicted, CNBR2 polypeptide, containing a CN binding region with high affinity but lacking the DNA binding domain and the transactivation domain, acts in a dominant negative manner in mNF-ATx1-dependent reactions.

What is claimed is:

1. A method for screening a compound that inhibits the interaction between calcineurin and NF-ATx, the method comprising:
 (a) contacting a polypeptide having calcineurin-binding activity selected from the group consisting of:
  (i) a polypeptide comprising a fragment of NF-AT3, wherein the fragment comprises the amino acid sequence set forth in SEQ ID NO: 2 or 4, up to but not including full length NF-AT3; and
  (ii) a polypeptide comprising a fragment of a NF-ATx family protein, wherein the fragment corresponds to the fragment of (i);
 with calcineurin in the presence or absence of a sample compound;
 (b) detecting the binding activity of the polypeptide to calcineurin; and
 (c) selecting a compound that reduces the binding activity compared with the binding activity detected in the absence of the sample compound.

2. The method of claim 1, wherein the polypeptide having calcineurin-binding activity is selected from the group consisting of:
 (i) a polypeptide comprising a fragment of NF-AT3, wherein the fragment comprises the amino acid sequence set forth in SEQ ID No: 2 or 4, but not including more than 50 amino acids of NF-AT3 outside of SEQ ID NO: 2 or 4; and
 (ii) a polypeptide comprising a fragment of a NF-ATx family protein, wherein the fragment corresponds to the fragment of (i).

3. The method of claim 1, wherein the polypeptide having calcineurin-binding activity is selected from the group consisting of:
 (i) a polypeptide comprising a fragment of NF-AT3, wherein the fragment comprises the amino acid sequence set forth in SEQ ID NO: 2 or 4, but not including more than 30 amino acids of NF-AT3 outside of SEQ ID NO: 2 or 4; and
 (ii) a polypeptide comprising a fragment of a NF-ATx family protein, wherein the fragment corresponds to the fragment of (i).

4. The method of claim 1, wherein the polypeptide having calcineurin-binding activity is selected from the group consisting of:
 (i) a polypeptide comprising a fragment of NF-AT3, wherein the fragment comprises the amino acid sequence set forth in SEQ ID No: 2 or 4, but not including more than 10 amino acids of NF-AT3 outside of SEQ ID NO: 2 or 4; and
 (ii) a polypeptide comprising a fragment of a NF-ATx family protein, wherein the fragment corresponds to the fragment of (i).

5. The method of claim 1, wherein the polypeptide having calcineurin-binding activity is selected from the group consisting of:
 (i) a polypeptide consisting of the amino acid sequence set forth in SEQ ID NO. 2 or 4; and
 (ii) a polypeptide comprising a fragment of a NF-ATx family protein,
 wherein the fragment corresponds to the polypeptide of (i).

6. The method of claim 1, wherein the polypeptide having calcineurin binding activity is a fusion polypeptide comprising a fragment of the NF-AT3 or the NF-ATx family protein fused sequentially with one or more other polypeptides.

* * * * *

SEQUENCE LISTING

<160> NUMBER OF SEQ ID NOS: 11

<210> SEQ ID NO 1
<211> LENGTH: 119
<212> TYPE: PRT
<213> ORGANISM: Mus musculus

```
<400> SEQUENCE: 1

Ala Pro Pro Pro Gly Ser Arg Pro Ala Asp Leu Glu Pro Asp Asp
 1               5                  10                  15

Cys Ala Ser Ile Tyr Ile Phe Asn Val Asp Pro Pro Ser Thr Leu
            20                  25                  30

Thr Thr Pro Leu Cys Leu Pro His His Gly Leu Pro Ser His Ser Ser
        35                  40                  45

Val Leu Ser Pro Ser Phe Gln Leu Gln Ser His Lys Asn Tyr Glu Gly
 50                  55                  60

Thr Cys Glu Ile Pro Glu Ser Lys Tyr Ser Pro Leu Gly Gly Pro Lys
 65                  70                  75                  80

Pro Phe Glu Cys Pro Ser Ile Gln Phe Thr Ser Ile Ser Pro Asn Cys
                85                  90                  95

Gln Gln Glu Leu Asp Ala His Glu Asp Asp Leu Gln Ile Asn Asp Pro
                100                 105                 110

Glu Arg Glu Phe Leu Glu Arg
                115

<210> SEQ ID NO 2
<211> LENGTH: 86
<212> TYPE: PRT
<213> ORGANISM: Mus musculus

<400> SEQUENCE: 2

Leu Ser Pro Ala Pro Phe Pro Phe Gln Tyr Cys Val Glu Thr Asp Ile
 1               5                  10                  15

Pro Leu Lys Thr Arg Lys Thr Ser Glu Asp Gln Ala Ala Ile Leu Pro
            20                  25                  30

Gly Lys Leu Glu Ile Cys Ser Asp Asp Gln Gly Asn Leu Ser Pro Ser
        35                  40                  45

Arg Glu Thr Ser Val Asp Asp Gly Leu Gly Ser Gln Tyr Pro Leu Lys
 50                  55                  60

Lys Asp Ser Ser Gly Asp Gln Phe Leu Ser Val Pro Ser Pro Phe Thr
 65                  70                  75                  80

Trp Ser Lys Pro Lys Pro
                85

<210> SEQ ID NO 3
<211> LENGTH: 123
<212> TYPE: PRT
<213> ORGANISM: Homo sapiens

<400> SEQUENCE: 3

Asp Gly Ala Pro Ala Pro Pro Pro Gly Ser Arg Pro Ala Asp Leu
 1               5                  10                  15

Glu Pro Asp Asp Cys Ala Ser Ile Tyr Ile Phe Asn Val Asp Pro Pro
            20                  25                  30

Pro Ser Thr Leu Thr Thr Pro Leu Cys Leu Pro His His Gly Leu Pro
        35                  40                  45

Ser His Ser Ser Val Leu Ser Pro Ser Phe Gln Leu Gln Ser His Lys
 50                  55                  60

Asn Tyr Glu Gly Thr Cys Glu Ile Pro Glu Ser Lys Tyr Ser Pro Leu
 65                  70                  75                  80

Gly Gly Pro Lys Pro Phe Glu Cys Pro Ser Ile Gln Ile Thr Ser Ile
                85                  90                  95
```

```
Ser Pro Asn Cys His Gln Glu Leu Asp Ala His Glu Asp Asp Leu Gln
            100                 105                 110

Ile Asn Asp Pro Glu Arg Glu Phe Leu Glu Arg
        115                 120
```

<210> SEQ ID NO 4
<211> LENGTH: 86
<212> TYPE: PRT
<213> ORGANISM: Homo sapiens

<400> SEQUENCE: 4

```
Leu Gly Pro Ala Val Phe Pro Phe Gln Tyr Cys Val Glu Thr Asp Ile
 1               5                  10                  15

Pro Leu Lys Thr Arg Lys Thr Ser Glu Asp Gln Ala Ala Ile Leu Pro
            20                  25                  30

Gly Lys Leu Glu Leu Cys Ser Asp Asp Gln Gly Ser Leu Ser Pro Ala
        35                  40                  45

Arg Glu Thr Ser Ile Asp Asp Gly Leu Gly Ser Gln Tyr Pro Leu Lys
    50                  55                  60

Lys Asp Ser Cys Gly Asp Gln Phe Leu Ser Val Pro Ser Pro Phe Thr
65                  70                  75                  80

Trp Ser Lys Pro Lys Pro
                85
```

<210> SEQ ID NO 5
<211> LENGTH: 559
<212> TYPE: PRT
<213> ORGANISM: Murine sp.

<400> SEQUENCE: 5

```
Met Thr Thr Ala Asn Cys Gly Ala His Asp Glu Leu Asp Phe Lys Leu
 1               5                  10                  15

Val Phe Gly Glu Asp Gly Ala Pro Ala Pro Pro Pro Gly Ser Arg
            20                  25                  30

Pro Ala Asp Leu Glu Pro Asp Asp Cys Ala Ser Ile Tyr Ile Phe Asn
        35                  40                  45

Val Asp Pro Pro Pro Ser Thr Leu Thr Thr Pro Leu Cys Leu Pro His
    50                  55                  60

His Gly Leu Pro Ser His Ser Ser Val Leu Ser Pro Ser Phe Gln Leu
65                  70                  75                  80

Gln Ser His Lys Asn Tyr Glu Gly Thr Cys Glu Ile Pro Glu Ser Lys
            85                  90                  95

Tyr Ser Pro Leu Gly Gly Pro Lys Pro Phe Glu Cys Pro Ser Ile Gln
            100                 105                 110

Phe Thr Ser Ile Ser Pro Asn Cys Gln Gln Glu Leu Asp Ala His Glu
        115                 120                 125

Asp Asp Leu Gln Ile Asn Asp Pro Glu Arg Glu Phe Leu Glu Arg Pro
    130                 135                 140

Ser Arg Asp His Leu Tyr Leu Pro Leu Glu Pro Ser Tyr Arg Glu Ser
145                 150                 155                 160

Ser Leu Ser Pro Ser Pro Ala Ser Ser Ile Ser Ser Arg Ser Trp Phe
            165                 170                 175

Ser Asp Ala Ser Ser Cys Glu Ser Leu Ser His Ile Tyr Asp Asp Val
        180                 185                 190

Asp Ser Glu Leu Asn Glu Ala Ala Ala Arg Phe Thr Leu Gly Ser Pro
    195                 200                 205
```

-continued

```
Leu Thr Ser Pro Gly Gly Ser Pro Gly Gly Cys Pro Gly Glu Glu Ser
        210                 215                 220

Trp His Gln Gln Tyr Gly Ser Gly His Ser Leu Ser Pro Arg Gln Ser
225                 230                 235                 240

Pro Cys His Ser Pro Arg Ser Ser Ile Thr Asp Glu Asn Trp Leu Ser
                245                 250                 255

Pro Arg Pro Ala Ser Gly Pro Ser Ser Arg Pro Thr Ser Pro Cys Gly
                260                 265                 270

Lys Arg Arg His Ser Ser Ala Glu Val Cys Tyr Ala Gly Ser Leu Ser
            275                 280                 285

Pro His His Ser Pro Val Pro Ser Pro Gly His Ser Pro Arg Gly Ser
        290                 295                 300

Val Thr Glu Asp Thr Trp Leu Thr Ala Pro Val His Thr Gly Ser Gly
305                 310                 315                 320

Leu Ser Pro Ala Pro Phe Pro Phe Gln Tyr Cys Val Glu Thr Asp Ile
                325                 330                 335

Pro Leu Lys Thr Arg Lys Thr Ser Glu Asp Gln Ala Ala Ile Leu Pro
                340                 345                 350

Gly Lys Leu Glu Ile Cys Ser Asp Asp Gln Gly Asn Leu Ser Pro Ser
            355                 360                 365

Arg Glu Thr Ser Val Asp Asp Gly Leu Gly Ser Gln Tyr Pro Leu Lys
        370                 375                 380

Lys Asp Ser Ser Gly Asp Gln Phe Leu Ser Val Pro Ser Pro Phe Thr
385                 390                 395                 400

Trp Ser Lys Pro Lys Pro Gly His Thr Pro Ile Phe Arg Thr Ser Ser
                405                 410                 415

Leu Pro Pro Leu Asp Trp Pro Leu Pro Thr His Phe Gly Gln Cys Glu
                420                 425                 430

Leu Lys Ile Glu Val Gln Pro Lys Thr His His Arg Ala His Tyr Glu
            435                 440                 445

Thr Glu Gly Ser Arg Gly Ala Val Lys Ala Ser Thr Gly Gly His Pro
        450                 455                 460

Val Val Lys Leu Leu Gly Tyr Ser Glu Lys Pro Ile Asn Leu Gln Met
465                 470                 475                 480

Phe Ile Gly Thr Ala Asp Asp Arg Tyr Leu Arg Pro His Ala Phe Tyr
                485                 490                 495

Gln Val His Arg Ile Thr Gly Lys Thr Val Ala Thr Ala Ser Gln Glu
                500                 505                 510

Ile Ile Ile Ala Ser Thr Lys Val Leu Glu Ile Pro Leu Leu Pro Glu
            515                 520                 525

Asn Asn Met Ser Ala Ser Ile Asp Cys Ala Gly Ile Leu Lys Leu Arg
        530                 535                 540

Asn Ser Asp Ile Glu Leu Arg Lys Gly Glu Thr Asp Ile Gly Arg
545                 550                 555
```

<210> SEQ ID NO 6
<211> LENGTH: 559
<212> TYPE: PRT
<213> ORGANISM: Homo sapiens
<400> SEQUENCE: 6

```
Met Thr Thr Ala Asn Cys Gly Ala His Asp Glu Leu Asp Phe Lys Leu
  1               5                  10                  15

Val Phe Gly Glu Asp Gly Ala Pro Ala Pro Pro Pro Gly Ser Arg
            20                  25                  30
```

-continued

```
Pro Ala Asp Leu Glu Pro Asp Asp Cys Ala Ser Ile Tyr Ile Phe Asn
            35                  40                  45

Val Asp Pro Pro Ser Thr Leu Thr Thr Pro Leu Cys Leu Pro His
    50                  55                  60

His Gly Leu Pro Ser His Ser Ser Val Leu Ser Pro Ser Phe Gln Leu
65                  70                  75                  80

Gln Ser His Lys Asn Tyr Glu Gly Thr Cys Glu Ile Pro Glu Ser Lys
                85                  90                  95

Tyr Ser Pro Leu Gly Pro Lys Pro Phe Glu Cys Pro Ser Ile Gln
            100                 105                 110

Ile Thr Ser Ile Ser Pro Asn Cys His Gln Glu Leu Asp Ala His Glu
            115                 120                 125

Asp Asp Leu Gln Ile Asn Asp Pro Glu Arg Glu Phe Leu Glu Arg Pro
    130                 135                 140

Ser Arg Asp His Leu Tyr Leu Pro Leu Glu Pro Ser Tyr Arg Glu Ser
145                 150                 155                 160

Ser Leu Ser Pro Ser Pro Ala Ser Ser Ile Ser Ser Arg Ser Trp Phe
                165                 170                 175

Ser Asp Ala Ser Ser Cys Glu Ser Leu Ser His Ile Tyr Asp Asp Val
            180                 185                 190

Asp Ser Glu Leu Asn Glu Ala Ala Ala Arg Phe Thr Leu Gly Ser Pro
            195                 200                 205

Leu Thr Ser Pro Gly Gly Ser Pro Gly Gly Cys Pro Gly Glu Glu Thr
    210                 215                 220

Trp His Gln Gln Tyr Gly Leu Gly His Ser Leu Ser Pro Arg Gln Ser
225                 230                 235                 240

Pro Cys His Ser Pro Arg Ser Ser Val Thr Asp Glu Asn Trp Leu Ser
                245                 250                 255

Pro Arg Pro Ala Ser Gly Pro Ser Ser Arg Pro Thr Ser Pro Cys Gly
            260                 265                 270

Lys Arg Arg His Ser Ser Ala Glu Val Cys Tyr Ala Gly Ser Leu Ser
275                 280                 285

Pro His His Ser Pro Val Pro Ser Pro Gly His Ser Pro Arg Gly Ser
    290                 295                 300

Val Thr Glu Asp Thr Trp Leu Asn Ala Ser Val His Gly Gly Ser Gly
305                 310                 315                 320

Leu Gly Pro Ala Val Phe Pro Phe Gln Tyr Cys Val Glu Thr Asp Ile
                325                 330                 335

Pro Leu Lys Thr Arg Lys Thr Ser Glu Asp Gln Ala Ala Ile Leu Pro
            340                 345                 350

Gly Lys Leu Glu Leu Cys Ser Asp Asp Gln Gly Ser Leu Ser Pro Ala
        355                 360                 365

Arg Glu Thr Ser Ile Asp Asp Gly Leu Gly Ser Gln Tyr Pro Leu Lys
    370                 375                 380

Lys Asp Ser Cys Gly Asp Gln Phe Leu Ser Val Pro Ser Pro Phe Thr
385                 390                 395                 400

Trp Ser Lys Pro Lys Pro Gly His Thr Pro Ile Phe Arg Thr Ser Ser
                405                 410                 415

Leu Pro Pro Leu Asp Trp Pro Leu Pro Ala His Phe Gly Gln Cys Glu
            420                 425                 430

Leu Lys Ile Glu Val Gln Pro Lys Thr His His Arg Ala His Tyr Glu
        435                 440                 445
```

-continued

```
Thr Glu Gly Ser Arg Gly Ala Val Lys Ala Ser Thr Gly Gly His Pro
    450                 455                 460
Val Val Lys Leu Leu Gly Tyr Asn Glu Lys Pro Ile Asn Leu Gln Met
465                 470                 475                 480
Phe Ile Gly Thr Ala Asp Asp Arg Tyr Leu Arg Pro His Ala Phe Tyr
                485                 490                 495
Gln Val His Arg Ile Thr Gly Lys Thr Val Ala Thr Ala Ser Gln Glu
            500                 505                 510
Ile Ile Ile Ala Ser Thr Lys Val Leu Glu Ile Pro Leu Leu Pro Glu
        515                 520                 525
Asn Asn Met Ser Ala Ser Ile Asp Cys Ala Gly Ile Leu Lys Leu Arg
    530                 535                 540
Asn Ser Asp Ile Glu Leu Arg Lys Gly Glu Thr Asp Ile Gly Arg
545                 550                 555
```

<210> SEQ ID NO 7
<211> LENGTH: 549
<212> TYPE: PRT
<213> ORGANISM: Artificial Sequence
<220> FEATURE:
<223> OTHER INFORMATION: Description of Artificial Sequence: Murine/
      Human NFATc3

<400> SEQUENCE: 7

```
Pro Arg Arg Val Leu Phe Ser Val Ser Ala Gln Leu Pro Ser Arg Thr
  1               5                  10                  15
Arg Pro Gly Pro Ser Asp Leu Asp Leu Glu Pro Asp Asp Cys Ala Ser
                20                  25                  30
Ile Tyr Ile Phe Asn Val Asp Pro Pro Ser Thr Leu Asn Ser Ser
            35                  40                  45
Leu Gly Leu Pro His His Gly Leu Leu Gln Ser His Ser Ser Val Leu
     50                  55                  60
Ser Pro Ser Phe Gln Leu Gln Gly Tyr Lys Asn Tyr Glu Gly Thr Gly
 65                  70                  75                  80
Asp Ile Ser Glu Ser Lys Tyr Ser Pro Leu Gly Gly Pro Lys Pro Phe
                85                  90                  95
Glu Cys Pro Ser Ile Gln Ile Thr Ser Ile Ser Pro Asn Cys His Gln
            100                 105                 110
Gly Thr Asp Ala His Glu Asp Leu His Ile Asn Asp Pro Glu Arg
        115                 120                 125
Glu Tyr Leu Glu Arg Pro Ser Arg Asp His Leu Tyr Leu Pro Leu Glu
    130                 135                 140
Pro Ser Tyr Arg Glu Ser Ser Leu Ser Pro Ser Pro Ala Ser Ser Ile
145                 150                 155                 160
Ser Ser Arg Ser Trp Phe Ser Asp Ala Ser Ser Cys Glu Ser Leu Ser
                165                 170                 175
His Ile Tyr Asp Asp Val Asp Ser Glu Leu Asn Glu Ala Ala Ala Arg
            180                 185                 190
Phe Thr Leu Gly Ser Pro Leu Thr Ser Pro Gly Gly Ser Pro Gly Gly
        195                 200                 205
Cys Pro Gly Glu Glu Ser Trp His Gln Gln Tyr Gly Ser Gly His Ser
    210                 215                 220
Leu Ser Pro Arg Gln Ser Pro Cys His Ser Pro Arg Ser Ser Ile Thr
225                 230                 235                 240
Asp Glu Asn Trp Leu Ser Pro Arg Pro Ala Ser Gly Pro Ser Ser Arg
                245                 250                 255
```

-continued

```
Pro Thr Ser Pro Cys Gly Lys Arg Arg His Ser Ser Ala Glu Val Cys
            260                 265                 270

Tyr Ala Gly Ser Leu Ser Pro His His Ser Pro Val Pro Ser Pro Gly
        275                 280                 285

His Ser Pro Arg Gly Ser Val Thr Glu Asp Thr Trp Leu Thr Ala Pro
    290                 295                 300

Val His Thr Gly Ser Gly Leu Ser Pro Ala Pro Phe Pro Phe Gln Tyr
305                 310                 315                 320

Cys Val Glu Thr Asp Ile Pro Leu Lys Thr Arg Lys Thr Ser Glu Asp
                325                 330                 335

Gln Ala Ala Ile Leu Pro Gly Lys Leu Glu Ile Cys Ser Asp Asp Gln
            340                 345                 350

Gly Asn Leu Ser Pro Ser Arg Glu Thr Ser Val Asp Asp Gly Leu Gly
        355                 360                 365

Ser Gln Tyr Pro Leu Lys Lys Asp Ser Ser Gly Asp Gln Phe Leu Ser
    370                 375                 380

Val Pro Ser Pro Phe Thr Trp Ser Lys Pro Lys Pro Gly His Thr Pro
385                 390                 395                 400

Ile Phe Arg Thr Ser Ser Leu Pro Pro Leu Asp Trp Pro Leu Pro Thr
                405                 410                 415

His Phe Gly Gln Cys Glu Leu Lys Ile Glu Val Gln Pro Lys Thr His
            420                 425                 430

His Arg Ala His Tyr Glu Thr Glu Gly Ser Arg Gly Ala Val Lys Ala
        435                 440                 445

Ser Thr Gly Gly His Pro Val Val Lys Leu Leu Gly Tyr Ser Glu Lys
    450                 455                 460

Pro Ile Asn Leu Gln Met Phe Ile Gly Thr Ala Asp Asp Arg Tyr Leu
465                 470                 475                 480

Arg Pro His Ala Phe Tyr Gln Val His Arg Ile Thr Gly Lys Thr Val
                485                 490                 495

Ala Thr Ala Ser Gln Glu Ile Ile Ile Ala Ser Thr Lys Val Leu Glu
            500                 505                 510

Ile Pro Leu Leu Pro Glu Asn Asn Met Ser Ala Ser Ile Asp Cys Ala
        515                 520                 525

Gly Ile Leu Lys Leu Arg Asn Ser Asp Ile Glu Leu Arg Lys Gly Glu
    530                 535                 540

Thr Asp Ile Gly Arg
545
```

<210> SEQ ID NO 8
<211> LENGTH: 395
<212> TYPE: PRT
<213> ORGANISM: Homo sapiens

<400> SEQUENCE: 8

```
Met Asn Ala Pro Glu Arg Gln Pro Gln Pro Asp Gly Gly Asp Ala Pro
1               5                   10                  15

Gly His Glu Pro Gly Gly Ser Pro Gln Asp Glu Leu Asp Phe Ser Ile
            20                  25                  30

Leu Phe Asp Tyr Glu Tyr Leu Asn Pro Asn Glu Glu Pro Asn Ala
        35                  40                  45

His Lys Val Ala Ser Pro Pro Ser Gly Pro Ala Tyr Pro Asp Asp Val
    50                  55                  60

Met Asp Tyr Gly Leu Lys Pro Tyr Ser Pro Leu Ala Ser Leu Ser Gly
```

-continued

```
                65                  70                  75                  80
Glu Pro Pro Gly Arg Phe Gly Glu Pro Asp Arg Val Gly Pro Gln Lys
                        85                  90                  95

Phe Leu Ser Ala Ala Lys Pro Ala Gly Ala Ser Gly Leu Ser Pro Arg
                100                 105                 110

Ile Glu Ile Thr Pro Ser His Glu Leu Ile Gln Ala Val Gly Pro Leu
                115                 120                 125

Arg Met Arg Asp Ala Gly Leu Leu Val Glu Gln Pro Pro Leu Ala Gly
            130                 135                 140

Val Ala Ala Ser Pro Arg Phe Thr Leu Pro Val Pro Gly Phe Glu Gly
145                 150                 155                 160

Tyr Arg Glu Pro Leu Cys Leu Ser Pro Ala Ser Ser Gly Ser Ser Ala
                    165                 170                 175

Ser Phe Ile Ser Asp Thr Phe Ser Pro Tyr Thr Ser Pro Cys Val Ser
                180                 185                 190

Pro Asn Asn Gly Gly Pro Asp Asp Leu Cys Pro Gln Phe Gln Asn Ile
            195                 200                 205

Pro Ala His Tyr Ser Pro Arg Thr Ser Pro Ile Met Ser Pro Arg Thr
        210                 215                 220

Ser Leu Ala Glu Asp Ser Cys Leu Gly Arg His Ser Pro Val Pro Arg
225                 230                 235                 240

Pro Ala Ser Arg Ser Ser Ser Pro Gly Ala Lys Arg Arg His Ser Cys
                    245                 250                 255

Ala Glu Ala Leu Val Ala Leu Pro Pro Gly Ala Ser Pro Gln Arg Ser
                260                 265                 270

Arg Ser Pro Ser Pro Gln Pro Ser Ser His Val Ala Pro Gln Asp His
            275                 280                 285

Gly Ser Pro Ala Gly Tyr Pro Pro Val Ala Gly Ser Ala Val Ile Met
        290                 295                 300

Asp Ala Leu Asn Ser Leu Ala Thr Asp Ser Pro Cys Gly Ile Pro Pro
305                 310                 315                 320

Lys Met Trp Lys Thr Ser Pro Asp Pro Ser Pro Val Ser Ala Ala Pro
                    325                 330                 335

Ser Lys Ala Gly Leu Pro Arg His Ile Tyr Pro Ala Val Glu Phe Leu
                340                 345                 350

Gly Pro Cys Glu Gln Gly Glu Arg Arg Asn Ser Ala Pro Glu Ser Ile
            355                 360                 365

Leu Leu Val Pro Pro Thr Trp Pro Lys Pro Leu Val Pro Ala Ile Pro
        370                 375                 380

Ile Cys Ser Ile Pro Val Thr Ala Ser Leu Pro
385                 390                 395
```

<210> SEQ ID NO 9
<211> LENGTH: 413
<212> TYPE: PRT
<213> ORGANISM: Homo sapiens

<400> SEQUENCE: 9

```
Met Pro Ser Thr Ser Phe Pro Val Pro Ser Lys Phe Pro Leu Gly Pro
1               5                   10                  15

Ala Ala Ala Val Phe Gly Arg Gly Glu Thr Leu Gly Pro Ala Pro Arg
                20                  25                  30

Ala Gly Gly Thr Met Lys Ser Ala Glu Glu His Tyr Gly Tyr Ala
            35                  40                  45
```

```
Ser Ser Asn Val Ser Pro Ala Leu Pro Leu Pro Thr Ala His Ser Thr
     50                  55                  60

Leu Pro Ala Pro Cys His Asn Leu Gln Thr Ser Thr Pro Gly Ile Ile
 65              70                  75                      80

Pro Pro Ala Asp His Pro Ser Gly Tyr Gly Ala Ala Leu Asp Gly Gly
                 85                  90                  95

Pro Ala Gly Tyr Phe Leu Ser Ser Gly His Thr Arg Pro Asp Gly Ala
                100                 105                 110

Pro Ala Leu Glu Ser Pro Arg Ile Glu Ile Thr Ser Cys Leu Gly Leu
            115                 120                 125

Tyr His Asn Asn Asn Gln Phe Phe His Asp Val Glu Val Glu Asp Val
    130                 135                 140

Leu Pro Ser Ser Lys Arg Ser Pro Ser Thr Ala Thr Leu Ser Leu Pro
145                 150                 155                 160

Ser Leu Glu Ala Tyr Arg Asp Pro Ser Cys Leu Ser Pro Ala Ser Ser
                165                 170                 175

Leu Ser Ser Arg Ser Cys Asn Ser Glu Ala Ser Ser Tyr Glu Ser Asn
                180                 185                 190

Tyr Ser Tyr Pro Tyr Ala Ser Pro Gln Thr Ser Pro Trp Gln Ser Pro
        195                 200                 205

Cys Val Ser Pro Lys Thr Thr Asp Pro Glu Glu Gly Phe Pro Arg Gly
210                 215                 220

Leu Gly Ala Cys Thr Leu Leu Gly Ser Pro Gln His Ser Pro Ser Thr
225                 230                 235                 240

Ser Pro Arg Ala Ser Val Thr Glu Glu Ser Trp Leu Gly Ala Arg Ser
                245                 250                 255

Ser Arg Pro Ala Ser Pro Cys Asn Lys Arg Lys Tyr Ser Leu Asn Gly
            260                 265                 270

Arg Gln Pro Pro Tyr Ser Pro His His Ser Pro Thr Pro Ser Pro His
        275                 280                 285

Gly Ser Pro Arg Val Ser Val Thr Asp Asp Ser Trp Leu Gly Asn Thr
        290                 295                 300

Thr Gln Tyr Thr Ser Ser Ala Ile Val Ala Ala Ile Asn Ala Leu Thr
305                 310                 315                 320

Thr Asp Ser Ser Leu Asp Leu Gly Asp Gly Val Pro Val Lys Ser Arg
                325                 330                 335

Lys Thr Thr Leu Glu Gln Pro Pro Ser Val Ala Leu Lys Val Glu Pro
            340                 345                 350

Val Gly Glu Asp Leu Gly Ser Pro Pro Pro Ala Asp Phe Ala Pro
            355                 360                 365

Glu Asp Tyr Ser Ser Phe Gln His Ile Arg Lys Gly Gly Phe Cys Asp
    370                 375                 380

Gln Tyr Leu Ala Val Pro Gln His Pro Tyr Gln Trp Ala Lys Pro Lys
385                 390                 395                 400

Pro Leu Ser Pro Thr Ser Tyr Met Ser Pro Thr Leu Pro
                405                 410
```

<210> SEQ ID NO 10
<211> LENGTH: 418
<212> TYPE: PRT
<213> ORGANISM: Homo sapiens

<400> SEQUENCE: 10

```
Met Thr Thr Ala Asn Cys Gly Ala His Asp Glu Leu Asp Phe Lys Leu
 1               5                  10                  15
```

-continued

```
Val Phe Gly Glu Asp Gly Ala Pro Ala Pro Pro Pro Gly Ser Arg
             20                  25                  30

Pro Ala Asp Leu Glu Pro Asp Asp Cys Ala Ser Ile Tyr Ile Phe Asn
         35                  40                  45

Val Asp Pro Pro Pro Ser Thr Leu Thr Thr Pro Leu Cys Leu Pro His
     50                  55                  60

His Gly Leu Pro Ser His Ser Ser Val Leu Ser Pro Ser Phe Gln Leu
 65                  70                  75                  80

Gln Ser His Lys Asn Tyr Glu Gly Thr Cys Glu Ile Pro Glu Ser Lys
                 85                  90                  95

Tyr Ser Pro Leu Gly Gly Pro Lys Pro Phe Glu Cys Pro Ser Ile Gln
            100                 105                 110

Ile Thr Ser Ile Ser Pro Asn Cys His Gln Glu Leu Asp Ala His Glu
        115                 120                 125

Asp Asp Leu Gln Ile Asn Asp Pro Glu Arg Glu Phe Leu Glu Arg Pro
    130                 135                 140

Ser Arg Asp His Leu Tyr Leu Pro Leu Glu Pro Ser Tyr Arg Glu Ser
145                 150                 155                 160

Ser Leu Ser Pro Ser Pro Ala Ser Ser Ile Ser Ser Arg Ser Trp Phe
                165                 170                 175

Ser Asp Ala Ser Ser Cys Glu Ser Leu Ser His Ile Tyr Asp Asp Val
            180                 185                 190

Asp Ser Glu Leu Asn Glu Ala Ala Arg Phe Thr Leu Gly Ser Pro
        195                 200                 205

Leu Thr Ser Pro Gly Gly Ser Pro Gly Gly Cys Pro Gly Glu Glu Thr
    210                 215                 220

Trp His Gln Gln Tyr Gly Leu Gly His Ser Leu Ser Pro Arg Gln Ser
225                 230                 235                 240

Pro Cys His Ser Pro Arg Ser Ser Val Thr Asp Glu Asn Trp Leu Ser
                245                 250                 255

Pro Arg Pro Ala Ser Gly Pro Ser Ser Arg Pro Thr Ser Pro Cys Gly
            260                 265                 270

Lys Arg Arg His Ser Ser Ala Glu Val Cys Tyr Ala Gly Ser Leu Ser
        275                 280                 285

Pro His His Ser Pro Val Pro Ser Pro Gly His Ser Pro Arg Gly Ser
    290                 295                 300

Val Thr Glu Asp Thr Trp Leu Asn Ala Ser Val His Gly Gly Ser Gly
305                 310                 315                 320

Leu Gly Pro Ala Val Phe Pro Phe Gln Tyr Cys Val Glu Thr Asp Ile
                325                 330                 335

Pro Leu Lys Thr Arg Lys Thr Ser Glu Asp Gln Ala Ala Ile Leu Pro
            340                 345                 350

Gly Lys Leu Glu Leu Cys Ser Asp Asp Gln Gly Ser Leu Ser Pro Ala
        355                 360                 365

Arg Glu Thr Ser Ile Asp Asp Gly Leu Gly Ser Gln Tyr Pro Leu Lys
    370                 375                 380

Lys Asp Ser Cys Gly Asp Gln Phe Leu Ser Val Pro Ser Pro Phe Thr
385                 390                 395                 400

Trp Ser Lys Pro Lys Pro Gly His Thr Pro Ile Phe Arg Thr Ser Ser
                405                 410                 415

Leu Pro
```

<210> SEQ ID NO 11
<211> LENGTH: 404
<212> TYPE: PRT
<213> ORGANISM: Homo sapiens

<400> SEQUENCE: 11

```
Met Gly Ala Ala Ser Cys Glu Asp Glu Glu Leu Glu Phe Lys Leu Val
  1               5                  10                  15

Phe Gly Glu Glu Lys Glu Ala Pro Pro Leu Gly Ala Gly Leu Gly
             20                  25                  30

Glu Glu Leu Asp Ser Glu Asp Ala Pro Pro Cys Cys Arg Leu Ala Leu
             35                  40                  45

Gly Glu Pro Pro Tyr Gly Ala Pro Ile Gly Ile Pro Arg Pro
         50                  55                  60

Pro Pro Pro Arg Pro Gly Met His Ser Pro Pro Arg Pro Ala Pro
 65                  70                  75                  80

Ser Pro Gly Thr Trp Glu Ser Gln Pro Ala Arg Ser Val Arg Leu Gly
             85                  90                  95

Gly Pro Gly Gly Gly Ala Gly Gly Ala Gly Gly Gly Arg Val Leu Glu
             100                 105                 110

Cys Pro Ser Ile Arg Ile Thr Ser Ile Ser Pro Thr Pro Glu Pro Pro
             115                 120                 125

Ala Ala Leu Glu Asp Asn Pro Asp Ala Trp Gly Asp Gly Ser Pro Arg
130                 135                 140

Asp Tyr Pro Pro Pro Glu Gly Phe Gly Gly Tyr Arg Glu Ala Gly Ala
145                 150                 155                 160

Gln Gly Gly Gly Ala Phe Phe Ser Pro Ser Pro Gly Ser Ser Ser Leu
             165                 170                 175

Ser Ser Trp Ser Phe Phe Ser Asp Ala Ser Asp Glu Ala Ala Leu Tyr
             180                 185                 190

Ala Ala Cys Asp Glu Val Glu Ser Glu Leu Asn Glu Ala Ala Ser Arg
             195                 200                 205

Phe Gly Leu Gly Ser Pro Leu Pro Ser Pro Arg Ala Ser Pro Arg Pro
             210                 215                 220

Trp Thr Pro Glu Asp Pro Trp Ser Leu Tyr Gly Pro Ser Pro Gly Gly
225                 230                 235                 240

Arg Gly Pro Glu Asp Ser Trp Leu Leu Leu Ser Ala Pro Gly Pro Thr
             245                 250                 255

Pro Ala Ser Pro Arg Pro Ala Ser Pro Cys Gly Lys Arg Arg Tyr Ser
             260                 265                 270

Ser Ser Gly Thr Pro Ser Ser Ala Ser Pro Ala Leu Ser Arg Arg Gly
             275                 280                 285

Ser Leu Gly Glu Glu Gly Ser Glu Pro Pro Pro Pro Leu Pro
             290                 295                 300

Leu Ala Arg Asp Pro Gly Ser Pro Gly Pro Phe Asp Tyr Val Gly Ala
305                 310                 315                 320

Pro Pro Ala Glu Ser Ile Pro Gln Lys Thr Arg Arg Thr Ser Ser Glu
             325                 330                 335

Gln Ala Val Ala Leu Pro Arg Ser Glu Glu Pro Ala Ser Cys Asn Gly
             340                 345                 350

Lys Leu Pro Leu Gly Ala Glu Ser Val Ala Pro Gly Gly Ser
             355                 360                 365

Arg Lys Glu Val Ala Gly Met Asp Tyr Leu Ala Val Pro Ser Pro Leu
370                 375                 380
```

```
-continued

Ala Trp Ser Lys Ala Arg Ile Gly Gly His Ser Pro Ile Phe Arg Thr
385                 390                 395                 400

Ser Ala Leu Pro
```